(12) United States Patent
Butora et al.

(10) Patent No.: US 7,632,821 B2
(45) Date of Patent: Dec. 15, 2009

(54) RIBONUCLEOSIDE CYCLIC ACETAL DERIVATIVES FOR THE TREATMENT OF RNA-DEPENDENT RNA VIRAL INFECTION

(75) Inventors: Gabor Butora, Martinsville, NJ (US); Kenneth Alan Koeplinger, Lansdale, PA (US); Malcolm MacCoss, Freehold, NJ (US); Daniel R. McMasters, New York, NY (US); David B. Olsen, Lansdale, PA (US); Lihu Yang, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 156 days.

(21) Appl. No.: 11/990,051

(22) PCT Filed: Aug. 4, 2006

(86) PCT No.: PCT/US2006/030549

§ 371 (c)(1),
(2), (4) Date: Feb. 1, 2008

(87) PCT Pub. No.: WO2007/021610

PCT Pub. Date: Feb. 22, 2007

(65) Prior Publication Data

US 2009/0099126 A1      Apr. 16, 2009

Related U.S. Application Data

(60) Provisional application No. 60/706,708, filed on Aug. 9, 2005.

(51) Int. Cl.
*A01N 43/04* (2006.01)
*A61K 31/70* (2006.01)

(52) U.S. Cl. .............................. 514/43; 514/45; 514/48; 514/49; 514/50; 514/51; 536/27.1; 536/27.13; 536/28.1

(58) Field of Classification Search ........................ None
See application file for complete search history.

(56) References Cited

U.S. PATENT DOCUMENTS 5,134,154 A    7/1992    Freedman et al.

OTHER PUBLICATIONS

Bartenschlager, R. "Candidate Targets for Hepatitis C Virus-Specific Antiviral Therapy", Intervirology, 1997, vol. 40, pp. 378-393.
Brass, V. et al. "Recent developments in target identification against hepatitis C virus", Expert Opin. Ther. Targets, 2004, vol. 8, pp. 295-307.
Crabb, C. "Hard-Won Advances Spark Excitement About Hepatitis C", Science, 2001, vol. 294, pp. 506-507.
Dymock, B. "Emerging therapies for hepatitis C virus infection", Emerging Drugs, 2001, vol. 6, pp. 13-42.

Dymock, B. et al. "Novel approaches to the treatment of hepatitis C virus infection", Antiviral Chemistry & Chemotherapy, 2000, vol. 11, pp. 79-96.
Eldrup, A. et al. "Structure-Activity Relationship of Purine Ribonucleosides for Inhibition of Hepatitis C Virus RNA-Dependent RNA Polymerase", J. Med. Chem., 2004, vol. 47, pp. 2283-2295.
Hampton A. et al. "Nucleotides. IV. Conversion of Ribonucleosides to New 2',3'-Ketal Derivatives", Journal of the American Chemical Society, 1965, vol. 87, pp. 5481-5487.
Hoffmann, P. et al. "Recent patents on experimental therapy for hepatitis C virus infection (1999-2002)", Expert. Opin. Ther. Patents, 2003, vol. 13, pp. 1707-1723.
Ishi, K. et al. "Expression of Hepatitis C Virus NS5B Protein: Characterization if Its RNA Polymerase Activity and RNA Binding", Hepatology, 1999, vol. 29, pp. 1227-1235.
Lauer, G. et al. "Hepatitis C Virus Infection", New England Journal of Medicine, 2001, vol. 345, pp. 41-52.
Lohmann, V. et al. "Biochemical and Kinetic Analyses of NS5B RNA-Dependent RNA Polymerase of the Hepatitis C Virus", Virology, 1998, vol. 249, pp. 108-118.
Moradpour, D. et al. "Current and evolving therapies for hepatitis C", European Journal of Gastroenterology & Hepatology, 1999, vol. 11, pp. 1199-1202.
Rosen, H. et al. "Hepatitis C virus: current understanding and prospects for future therapies", Molecular Medicine Today, 1999, vol. 5, pp. 393-399.
Walker, M. et al. "Promising candidates for the treatment of chronic hepatitis C", Expert Opin. Investig. Drugs, 2003, vol. 12, pp. 1269-1280.

*Primary Examiner*—Patrick T Lewis
(74) *Attorney, Agent, or Firm*—Kenneth R. Walton; Sheldon O. Heber; Philippe L. Durette

(57) ABSTRACT

The present invention provides ribonucleoside 2',3'-cyclic acetals of structural formula I which are precursors or prodrugs of inhibitors of RNA-dependent RNA viral polymerase. These compounds are precursors of inhibitors of RNA-dependent RNA viral replication and are useful for the treatment of RNA-dependent RNA viral infection. They are particularly useful as precursors or prodrugs of inhibitors of hepatitis C virus (HCV) NS5B polymerase, as precursors or prodrugs of inhibitors of HCV replication, and/or for the treatment of hepatitis C infection. The invention also describes pharmaceutical compositions containing such ribonucleoside 2',3'-cyclic acetals alone or in combination with other agents active against RNA-dependent RNA viral infection, in particular HCV infection. Also disclosed are methods of inhibiting RNA-dependent RNA polymerase, inhibiting RNA-dependent RNA viral replication, and/or treating RNA-dependent RNA viral infection with the ribonucleoside 2',3'-cyclic acetals of the present invention.

(I)

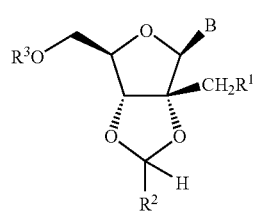

15 Claims, No Drawings

RIBONUCLEOSIDE CYCLIC ACETAL DERIVATIVES FOR THE TREATMENT OF RNA-DEPENDENT RNA VIRAL INFECTION

This application is the National Stage of International Application No. PCT/US2006/030549, filed on Aug. 4, 2006, which claims the benefit of U.S. Provisional Application No. 60/706,708 (filed Aug. 9, 2005), the disclosure of which is incorporated by reference herein in its entirety.

FIELD OF THE INVENTION

The present invention is concerned with 2',3'-cyclic acetals of ribonucleosides and certain analogs and derivatives thereof, their synthesis, and their use as precursors or prodrugs of inhibitors of RNA-dependent RNA viral polymerase. The compounds of the present invention are precursors or prodrugs of inhibitors of RNA-dependent RNA viral replication and are useful for the treatment of RNA-dependent RNA viral infection. They are particularly useful as precursors or prodrugs of inhibitors of hepatitis C virus (HCV) NS5B polymerase, as precursors or prodrugs of inhibitors of HCV replication, and for the treatment of hepatitis C viral infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 3.9 million infected people in the United States alone, according to the U.S. Center for Disease Control, roughly five times the number of people infected the human immunodeficiency virus (HIV). According to the World Health Organization, there are more than 170 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their off-spring. Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The state of the art in the treatment of HCV infection has been reviewed, and reference is made to the following publications: B. Dymock, et al., "Novel approaches to the treatment of hepatitis C virus infection," *Antiviral Chemistry & Chemotherapy*, 11: 79-96 (2000); H. Rosen, et al., "Hepatitis C virus: current understanding and prospects for future therapies," *Molecular Medicine Today*, 5: 393-399 (1999); D. Moradpour, et al., "Current and evolving therapies for hepatitis C," *European J. Gastroenterol. Hepatol.*, 11: 1189-1202 (1999); R. Bartenschlager, "Candidate Targets for Hepatitis C Virus-Specific Antiviral Therapy," *Intervirology*, 40: 378-393 (1997); G. M. Lauer and B. D. Walker, "Hepatitis C Virus Infection," *N. Engl. J. Med.*, 345: 41-52 (2001); B. W. Dymock, "Emerging therapies for hepatitis C virus infection," *Emerging Drugs*, 6: 13-42 (2001); and C. Crabb, "Hard-Won Advances Spark Excitement about Hepatitis C," *Science:* 506-507 (2001); the contents of all of which are incorporated by reference herein in their entirety.

Different approaches to HCV therapy have been taken, which include the inhibition of viral serine proteinase (NS3 protease), helicase, and RNA-dependent RNA polymerase (NS5B), and the development of a vaccine.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. NS5B polymerase is therefore considered to be an essential component in the HCV replication complex [see K. Ishi, et al., "Expression of Hepatitis C Virus NS5B Protein: Characterization of Its RNA Polymerase Activity and RNA Binding," *Hepatology*, 29: 1227-1235 (1999) and V. Lohmann, et al., "Biochemical and Kinetic Analyses of NS5B RNA-Dependent RNA Polymerase of the Hepatitis C Virus," *Virology*, 249: 108-118 (1998)]. Inhibition of HCV NS5B polymerase prevents formation of the double-stranded HCV RNA and therefore constitutes an attractive approach to the development of HCV-specific antiviral therapies.

The development of inhibitors of HCV NS5B polymerase with potential for the treatment of HCV infection has been reviewed in M. P. Walker et al., "Promising candidates for the treatment of chronic hepatitis C," *Expert Opin. Invest. Drugs*, 12: 1269-1280 (2003); P. Hoffmann et al., "Recent patents on experimental therapy for hepatitis C virus infection (1999-2002)," *Expert Opin. Ther. Patents,"* 13: 1707-1723 (2003); and V. Brass, et al., "Recent developments in target identification against HCV," *Expert Opin. Ther. Targets,"* 8: 295-307 (2004). Inhibition of HCV replication by purine ribonucleosides was reported by A. E. Eldrup, et al., in "Structure-Activity Relationship of Purine Ribonucleosides for Inhibition of HCV RNA-Dependent RNA Polymerase," *J. Med. Chem.*, 47: 2283-2295 (2004). There is a continuing need for structurally diverse nucleoside derivatives as inhibitors of HCV polymerase as therapeutic approaches for HCV therapy.

It has now been found that certain ribonucleoside 2',3'-cyclic acetals and analogs and derivatives thereof are precursors or prodrugs of potent inhibitors of RNA-dependent RNA viral replication and in particular HCV replication. The cyclic acetals are precursors or prodrugs of the ribonucleoside 2',3'-diol and their 5'-triphosphate derivatives which are inhibitors of RNA-dependent RNA viral polymerase and in particular HCV NS5B polymerase. The compounds of the present invention are therefore useful to treat RNA-dependent RNA viral infection and in particular HCV infection.

It is therefore an object of the present invention to provide ribonucleoside 2',3'-cyclic acetals and certain analogs and derivatives thereof which are useful as precursors or prodrugs of inhibitors of RNA-dependent RNA viral polymerase and in particular as precursors or prodrugs of inhibitors of HCV NS5B polymerase.

It is another object of the present invention to provide ribonucleoside 2',3'-cyclic acetals and certain analogs and derivatives thereof which are useful as precursors or prodrugs of inhibitors of the replication of an RNA-dependent RNA virus and in particular as precursors or prodrugs of inhibitors of the replication of hepatitis C virus.

It is another object of the present invention to provide ribonucleoside 2',3'-cyclic acetals and certain analogs and derivatives thereof which are useful in the treatment of RNA-dependent RNA viral infection and in particular in the treatment of HCV infection.

It is another object of the present invention to provide pharmaceutical compositions comprising the ribonucleoside 2',3'-cyclic acetals of the present invention and certain analogs and derivatives thereof in association with a pharmaceutically acceptable carrier.

It is another object of the present invention to provide pharmaceutical compositions comprising the ribonucleoside 2',3'-cyclic acetals of the present invention and certain analogs and derivatives thereof for use as precursors or prodrugs of inhibitors of RNA-dependent RNA viral polymerase and in particular as inhibitors of HCV NS5B polymerase.

It is another object of the present invention to provide pharmaceutical compositions comprising the ribonucleoside 2',3'-cyclic acetals of the present invention and certain analogs and derivatives thereof for use as precursors or prodrugs of inhibitors of RNA-dependent RNA viral replication and in particular as precursors or prodrugs of inhibitors of HCV replication.

It is another object of the present invention to provide pharmaceutical compositions comprising the ribonucleoside 2',3'-cyclic acetals of the present invention and certain analogs and derivatives thereof for use in the treatment of RNA-dependent RNA viral infection and in particular in the treatment of HCV infection.

It is another object of the present invention to provide pharmaceutical compositions comprising the ribonucleoside 2',3'-cyclic acetals of the present invention and certain analogs and derivatives thereof in combination with other agents active against an RNA-dependent RNA virus and in particular against HCV.

It is another object of the present invention to provide methods for the inhibition of RNA-dependent RNA viral polymerase and in particular for the inhibition of HCV NS5B polymerase.

It is another object of the present invention to provide methods for the inhibition of RNA-dependent RNA viral replication and in particular for the inhibition of HCV replication.

It is another object of the present invention to provide methods for the treatment of RNA-dependent RNA viral infection and in particular for the treatment of HCV infection.

It is another object of the present invention to provide methods for the treatment of RNA-dependent RNA viral infection in combination with other agents active against RNA-dependent RNA virus and in particular for the treatment of HCV infection in combination with other agents active against HCV.

It is another object of the present invention to provide ribonucleoside 2',3'-cyclic acetals of the present invention and certain analogs and derivatives thereof and their pharmaceutical compositions for use as a medicament for the inhibition of RNA-dependent RNA viral replication and/or the treatment of RNA-dependent RNA viral infection and in particular for the inhibition of HCV replication and/or the treatment of HCV infection.

It is another object of the present invention to provide for the use of the ribonucleoside 2',3'-cyclic acetals of the present invention and certain analogs and derivatives thereof and their pharmaceutical compositions for the manufacture of a medicament for the inhibition of RNA-dependent RNA viral replication and/or the treatment of RNA-dependent RNA viral infection and in particular for the inhibition of HCV replication and/or the treatment of HCV infection.

These and other objects will become readily apparent from the detailed description which follows.

SUMMARY OF THE INVENTION

The present invention relates to ribonucleoside 2',3'-cyclic acetals of structural formula I of the indicated stereochemical configuration:

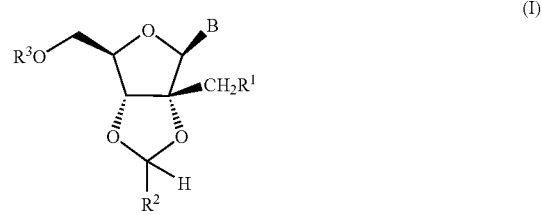

(I)

or a pharmaceutically acceptable salt thereof;

wherein B is

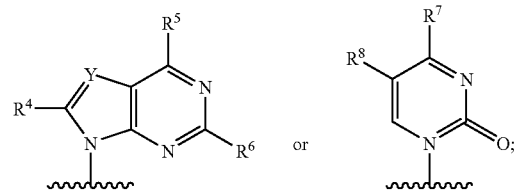

Y is N or $CR^{10}$;

$R^1$ is selected from the group consisting of hydrogen, fluoro, amino, hydroxy, and methoxy;

$R^2$ is selected from the group consisting of $C_{1-12}$ alkyl, $C_{3-8}$ cycloalkyl, aryl, and heteroaryl;

wherein alkyl and cycloalkyl are unsustituted or substituted with one to three substituents independently selected from halogen, hydroxy, carboxy, and $C_{1-4}$ alkoxy; and aryl and heteroaryl are unsubstituted or substituted with one to five substituents independently selected from $R^9$;

$R^3$ is selected from the group consisting of hydrogen, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, arylcarbonyl, aryloxycarbonyl, heteroarylcarbonyl, heteroaryloxycarbonyl, an amino acyl residue of structural formula:

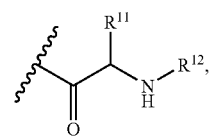

or a residue of structural formula:

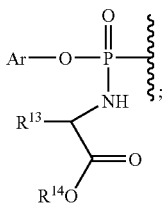

wherein alkylcarbonyl, alkyloxycarbonyl, cycloalkylcarbonyl, and cycloalkyloxycarbonyl are unsubstituted or substituted with one to three substituents independently selected from the group consisting of halogen, hydroxy, carboxy, $C_{1-4}$ alkoxy, amino, $C_{1-4}$ alkylamino, and di ($C_{1-4}$ alkyl)amino and wherein arylcarbonyl, aryloxycarbonyl, heteroarylcarbonyl, and heteroaryloxycarbonyl are unsubstituted or substituted with one to five substituents independently selected from $R^9$;

Ar is phenyl unsubstituted or substituted with one to three substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl;

$R^4$ is hydrogen, halogen, methyl, azido, cyano, or amino;

$R^5$, $R^6$, and $R^7$ are each independently hydroxy, halogen, amino, $C_{1-4}$ alkylamino, di($C_{1-4}$ alkyl)amino, $C_{3-6}$ cycloalkylamino, or di($C_{3-6}$ cycloalkyl)amino;

$R^8$ is hydrogen, $C_{1-3}$ alkyl, $C_{2-4}$ alkenyl, $C_{2-4}$ alkynyl, $C_{1-4}$ alkylamino, $CF_3$, or halogen;

each $R^9$ is independently selected from the group consisting of halogen, $C_{1-4}$ alkyl, $C_{1-4}$ alkoxy, $C_{1-4}$ alkylthio, $C_{1-4}$ alkylsulfonyl, cyano, nitro, amino, phenyl, carboxy, trifluoromethyl, difluoromethoxy, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl;

$R^{10}$ is hydrogen, fluorine, cyano, $C_{1-3}$ alkyl, $NHCONH_2$, $C(=O)NR^{15}R^{15}$, $C(=S)NR^{15}R^{15}$, $C(=O)OR^{15}$, $C(=NH)NH_2$, hydroxy, $C_{1-3}$ alkoxy, amino, $C_{1-4}$ alkylamino, di($C_{1-4}$ alkyl)amino, $C_{2-4}$ alkenyl, or $C_{2-4}$ alkynyl;

$R^{11}$ is hydrogen, $C_{1-5}$ alkyl, or phenyl $C_{0-2}$ alkyl;

$R^{12}$ is hydrogen, $C_{1-4}$ alkyl, $C_{1-4}$ acyl, benzoyl, $C_{1-4}$ alkyloxycarbonyl, phenyl $C_{0-2}$ alkyloxycarbonyl, $C_{1-4}$ alkylaminocarbonyl, phenyl $C_{0-2}$ alkylaminocarbonyl, $C_{1-4}$ alkylsulfonyl, or phenyl $C_{0-2}$ alkylsulfonyl;

$R^{13}$ is hydrogen, $C_{1-5}$ alkyl, phenyl or benzyl;
wherein alkyl is unsubstituted or substituted with one substituent selected from the group consisting of hydroxy, methoxy, amino, carboxy, carbamoyl, guanidino, mercapto, methylthio, 1H-imidazolyl, and 1H-indol-3-yl; and wherein phenyl and benzyl are unsubstituted or substituted with one to two substituents independently selected from the group consisting of halogen, hydroxy, and methoxy;

$R^{14}$ is hydrogen, $C_{1-6}$ alkyl, $C_{3-6}$ cycloalkyl, phenyl, or benzyl;
wherein alkyl and cycloalkyl are unsubstituted or substituted with one to three substituents independently selected from halogen, hydroxy, carboxy, $C_{1-4}$ alkoxy; and wherein phenyl and benzyl are unsubstituted or substituted with one to three substituents independently selected from halogen, hydroxy, cyano, $C_{1-4}$ alkoxy, and trifluoromethyl; and each $R^{15}$ is independently hydrogen or $C_{1-6}$ alkyl.

The compounds of formula I are useful as precursors or prodrugs of inhibitors of RNA-dependent RNA viral polymerase and in particular of HCV NS5B polymerase. They are also precursors or prodrugs of inhibitors of RNA-dependent RNA viral replication and in particular of HCV replication and are useful for the treatment of RNA-dependent RNA viral infection and in particular for the treatment of HCV infection.

Also encompassed within the present invention are pharmaceutical compositions containing the compounds alone or in combination with other agents active against RNA-dependent RNA virus and in particular against HCV as well as methods for the inhibition of RNA-dependent RNA viral replication and for the treatment of RNA-dependent RNA viral infection.

DETAILED DESCRIPTION OF THE INVENTION

The present invention relates to compounds of structural formula I of the indicated stereochemical configuration:

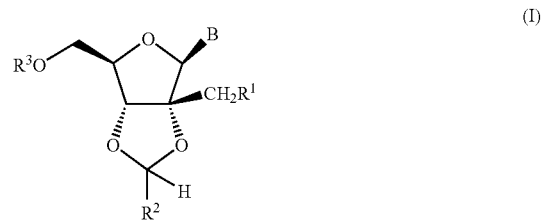

(I)

or a pharmaceutically acceptable salt thereof;
wherein B is

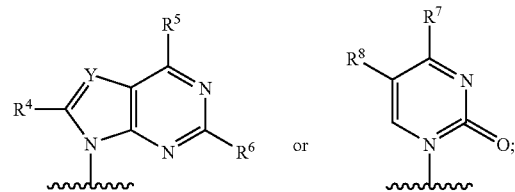

Y is N or $CR^{10}$;

$R^1$ is selected from the group consisting of hydrogen, fluoro, amino, hydroxy, and methoxy;

$R^2$ is selected from the group consisting of
$C_{1-12}$ alkyl,
$C_{3-8}$ cycloalkyl,
aryl, and
heteroaryl;
wherein alkyl and cycloalkyl are unsustituted or substituted with one to three substituents independently selected from halogen, hydroxy, carboxy, and $C_{1-4}$ alkoxy; and aryl and heteroaryl are unsubstituted or substituted with one to five substituents independently selected from $R^9$;

$R^3$ is selected from the group consisting of hydrogen, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, arylcarbonyl, aryloxycarbonyl, heteroarylcarbonyl, heteroaryloxycarbonyl, an amino acyl residue of structural formula:

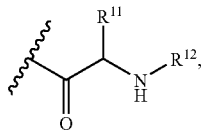

or a residue of structural formula:

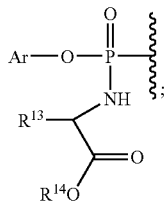

wherein alkylcarbonyl, alkyloxycarbonyl, cycloalkylcarbonyl, and cycloalkyloxycarbonyl are unsubstituted or substituted with one to three substituents independently selected from the group consisting of halogen, hydroxy, carboxy, $C_{1-4}$ alkoxy, amino, $C_{1-4}$ alkylamino, and di ($C_{1-4}$ alkyl)amino and wherein arylcarbonyl, aryloxycarbonyl, heteroarylcarbonyl, and heteroaryloxycarbonyl are unsubstituted or substituted with one to five substituents independently selected from $R^9$;

Ar is phenyl unsubstituted or substituted with one to three substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl;

$R^4$ is hydrogen, halogen, methyl, azido, cyano, or amino;

$R^5$, $R^6$, and $R^7$ are each independently hydroxy, halogen, amino, $C_{1-4}$ alkylamino, di($C_{1-4}$ alkyl)amino, $C_{3-6}$ cycloalkylamino, or di($C_{3-6}$ cycloalkyl)amino;

$R^8$ is hydrogen, $C_{1-3}$ alkyl, $C_{2-4}$ alkenyl, $C_{2-4}$ alkynyl, $C_{1-4}$ alkylamino, $CF_3$, or halogen; each $R^9$ is independently selected from the group consisting of halogen, $C_{1-4}$ alkyl, $C_{1-4}$ alkoxy, $C_{1-4}$ alkylthio, $C_{1-4}$ alkylsulfonyl, cyano, nitro, amino, phenyl, carboxy, trifluoromethyl, difluoromethoxy, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl;

$R^{10}$ is hydrogen, fluorine, cyano, $C_{1-3}$ alkyl, $NHCONH_2$, $C(=O)NR^{15}R^{15}$, $C(=S)NR^{15}R^{15}$, $C(=O)OR^{15}$, $C(=NH)NH_2$, hydroxy, $C_{1-3}$ alkoxy, amino, $C_{1-4}$ alkylamino, di($C_{1-4}$ alkyl)amino, $C_{2-4}$ alkenyl, or $C_{2-4}$ alkynyl;

$R^{11}$ is hydrogen, $C_{1-5}$ alkyl, or phenyl $C_{0-2}$ alkyl;

$R^{12}$ is hydrogen, $C_{1-4}$ alkyl, $C_{1-4}$ acyl, benzoyl, $C_{1-4}$ alkyloxycarbonyl, phenyl $C_{0-2}$ alkyloxycarbonyl, $C_{1-4}$ alkylaminocarbonyl, phenyl $C_{0-2}$ alkylaminocarbonyl, $C_{1-4}$ alkylsulfonyl, or phenyl $C_{0-2}$ alkylsulfonyl;

$R^{13}$ is hydrogen, $C_{1-5}$ alkyl, phenyl or benzyl;

wherein alkyl is unsubstituted or substituted with one substituent selected from the group consisting of hydroxy, methoxy, amino, carboxy, carbamoyl, guanidino, mercapto, methylthio, 1H-imidazolyl, and 1H-indol-3-yl; and wherein phenyl and benzyl are unsubstituted or substituted with one to two substituents independently selected from the group consisting of halogen, hydroxy, and methoxy;

$R^{14}$ is hydrogen, $C_{1-6}$ alkyl, $C_{3-6}$ cycloalkyl, phenyl, or benzyl;

wherein alkyl and cycloalkyl are unsubstituted or substituted with one to three substituents independently selected from halogen, hydroxy, carboxy, $C_{1-4}$ alkoxy; and wherein phenyl and benzyl are unsubstituted or substituted with one to three substituents independently selected from halogen, hydroxy, cyano, $C_{1-4}$ alkoxy, and trifluoromethyl; and each $R^{15}$ is independently hydrogen or $C_{1-6}$ alkyl.

The compounds of formula I are metabolized in the host to the corresponding ribonucleoside 5'-triphosphates which are inhibitors of RNA-dependent RNA viral polymerase. The compounds of formula I are useful as precursors or prodrugs of inhibitors of RNA-dependent RNA viral replication and for the treatment of RNA-dependent RNA viral infection. In particular, they are useful for the treatment of HCV infection.

In one embodiment of the compounds of the present invention, B is a purine base of the structural formula:

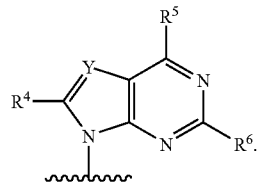

In a class of this embodiment, Y is N. In a subclass of this class, $R^4$ and $R^6$ are hydrogen and $R^5$ is amino. In another class of this embodiment, Y is $CR^{10}$. In a subclass of this class, $R^{10}$ is hydrogen or fluoro, $R^4$ and $R^6$ are hydrogen, and $R^5$ is amino.

In another embodiment, B is a pyrimidine base of the structural formula:

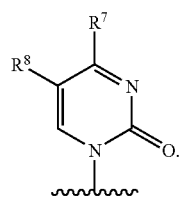

In a class of this second embodiment, $R^8$ is hydrogen and $R^7$ is amino.

In a third embodiment of the compounds of the present invention, $R^2$ is phenyl or naphthyl unsubstituted or substituted with one to three substituents independently selected from $R^9$. In a class of this embodiment, $R^2$ is phenyl unsubstituted or substituted with one to three substituents independently selected from $R^9$.

In a fourth embodiment of the compounds of the present invention, $R^2$ is $C_{1-6}$ alkyl unsustituted or substituted with one to three substituents independently selected from fluoro, hydroxy, carboxy, and $C_{1-4}$ alkoxy.

In a fifth embodiment of the compounds of the present invention, $R^3$ is hydrogen, $C_{1-6}$ alkylcarbonyl, $C_{3-6}$ cycloalkylcarbonyl, phenylcarbonyl, or heteroarylcarbonyl wherein phenylcarbonyl and heteroarylcarbonyl are unsubstituted or substituted with one to three substituents independently selected from $R^9$ and wherein alkylcarbonyl and cycloalkylcarbonyl are unsubstituted or substituted with one to three substituents independently selected from fluorine, hydroxy, carboxy, $C_{1-4}$ alkoxy, amino, $C_{1-4}$ alkylamino, and di ($C_{1-4}$ alkyl)amino.

In a sixth embodiment of the compounds of the present invention, $R^1$ is hydrogen or fluoro. In a class of this embodiment, $R^1$ is hydrogen.

Illustrative, but nonlimiting, examples of compounds of the present invention of structural formula I which are useful as precursors or prodrugs of inhibitors of RNA-dependent RNA viral polymerase are the following:

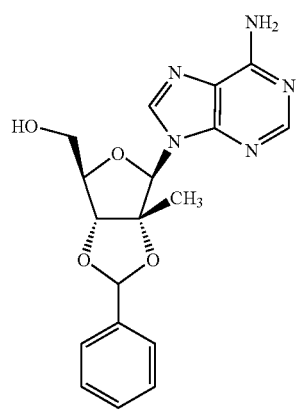

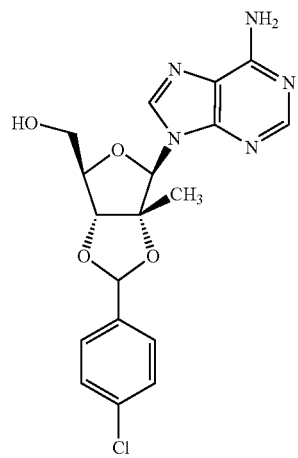

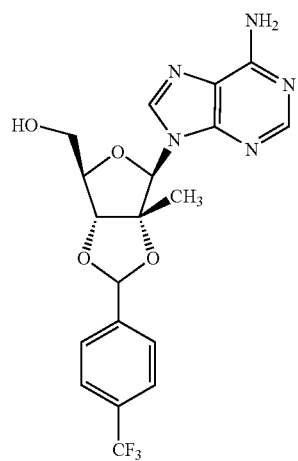

-continued

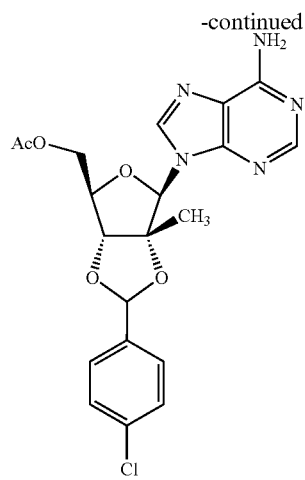

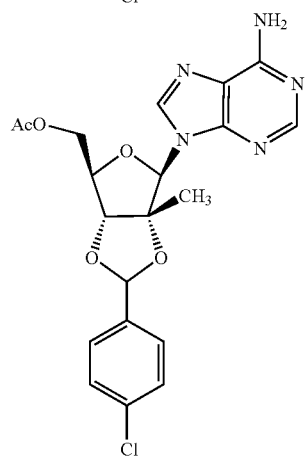

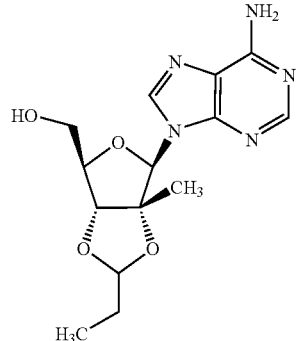

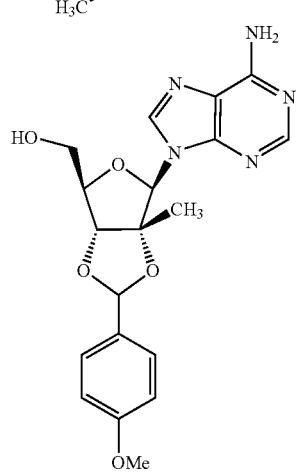

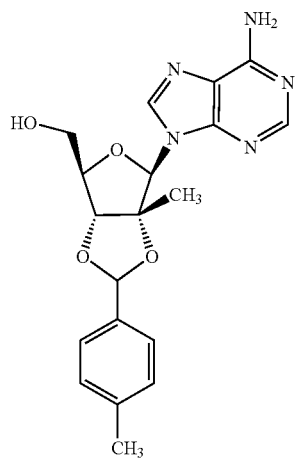
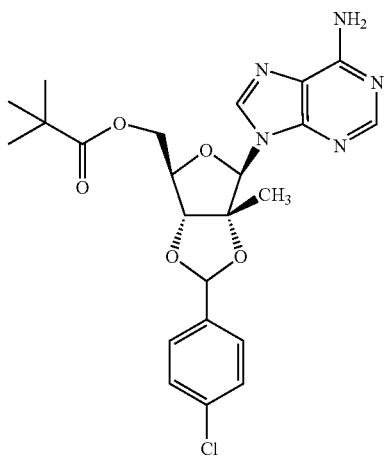
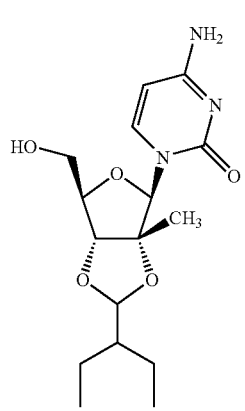
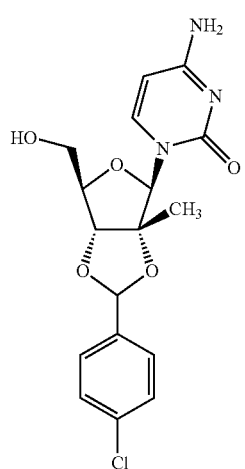

-continued

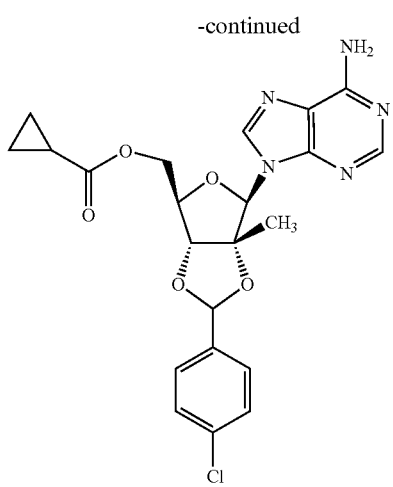

and pharmaceutically acceptable salts thereof.

In one embodiment of the present invention, the ribonucleoside 2',3'-cyclic acetals of the present invention are useful as precursors or prodrugs of inhibitors of positive-sense single-stranded RNA-dependent RNA viral polymerase, as precursors or prodrugs of inhibitors of positive-sense single-stranded RNA-dependent RNA viral replication, and/or for the treatment of positive-sense single-stranded RNA-dependent RNA viral infection. In a class of this embodiment, the positive-sense single-stranded RNA-dependent RNA virus is a Flaviviridae virus or a Picornaviridae virus. In a subclass of this class, the Picorizaviridae virus is a rhinovirus, a poliovirus, or a hepatitis A virus. In a second subclass of this class, the Flaviviridae virus is selected from the group consisting of hepatitis C virus, yellow fever virus, dengue virus, West Nile virus, Japanese encephalitis virus, Banzi virus, and bovine viral diarrhea virus (BVDV). In a subclass of this subclass, the Flaviviridae virus is hepatitis C virus.

Another aspect of the present invention is concerned with a method for inhibiting RNA-dependent RNA viral polymerase, a method for inhibiting RNA-dependent RNA viral replication, and/or a method for treating RNA-dependent RNA viral infection in a mammal in need thereof comprising administering to the mammal a therapeutically effective amount of a compound of structural formula I.

In one embodiment of this aspect of the present invention, the RNA-dependent RNA viral polymerase is a positive-sense single-stranded RNA-dependent RNA viral polymerase. In a class of this embodiment, the positive-sense single-stranded RNA-dependent RNA viral polymerase is a Flaviviridae viral polymerase or a Picornaviridae viral polymerase. In a subclass of this class, the Picorizaviridae viral polymerase is rhinovirus polymerase, poliovirus polymerase, or hepatitis A virus polymerase. In a second subclass of this class, the Flaviviridae viral polymerase is selected from the group consisting of hepatitis C virus polymerase, yellow fever virus polymerase, dengue virus polymerase, West Nile virus polymerase, Japanese encephalitis virus polymerase, Banzi virus polymerase, and bovine viral diarrhea virus (BVDV) polymerase. In a subclass of this subclass, the Flaviviridae viral polymerase is hepatitis C virus polymerase.

In a second embodiment of this aspect of the present invention, the RNA-dependent RNA viral replication is a positive-sense single-stranded RNA-dependent RNA viral replication. In a class of this embodiment, the positive-sense single-stranded RNA-dependent RNA viral replication is Flaviviridae viral replication or Picornaviridae viral replication. In a subclass of this class, the Picornaviridae viral replication is rhinovirus replication, poliovirus replication, or hepatitis A virus replication. In a second subclass of this class, the Flaviviridae viral replication is selected from the group consisting of hepatitis C virus replication, yellow fever virus replication, dengue virus replication, West Nile virus replication, Japanese encephalitis virus replication, Banzi virus replication, and bovine viral diarrhea virus replication. In a subclass of this subclass, the Flaviviridae viral replication is hepatitis C virus replication.

In a third embodiment of this aspect of the present invention, the RNA-dependent RNA viral infection is a positive-sense single-stranded RNA-dependent viral infection. In a class of this embodiment, the positive-sense single-stranded RNA-dependent RNA viral infection is Flaviviridae viral infection or Picornaviridae viral infection. In a subclass of this class, the Picornaviridae viral infection is rhinovirus infection, poliovirus infection, or hepatitis A virus infection. In a second subclass of this class, the Flaviviridae viral infection is selected from the group consisting of hepatitis C virus infection, yellow fever virus infection, dengue virus infection, West Nile virus infection, Japanese encephalitis virus infection, Banzi virus infection, and bovine viral diarrhea virus infection. In a subclass of this subclass, the Flaviviridae viral infection is hepatitis C virus infection.

Without being limited to a particular mechanism of action, the ribonucleoside 2',3'-cyclic acetals of formula I of the present invention exhibit targetted delivery of the anti-HCV ribonucleoside 2',3'-diols to the liver, the main organ of HCV infectivity. A goal of anti-HCV therapy with a nucleoside compound remains the selective delivery to the liver where the nucleoside compound can be converted into an inhibitor of HCV polymerase, namely the nucleoside 5'-triphosphate derivative. The ribonucleoside 2',3'-cyclic acetals of the present invention exhibit improved pharmacokinetic properties over the parent ribonucleoside, such as improved oral bioavailability. Once in the liver, the cyclic acetals can be selectively oxidized by the cytochrome P450 enzyme complex, in particular, the isozyme cytochrome CYP3A4, which is predominantly expressed in the liver. The oxidation is an NADPH-dependent process. The parent ribonucleoside is converted in the liver by ribonucleoside kinases into the biologically active ribonucleoside 5'-triphosphate, which can be detected in the liver of the host following the oral or parenteral administration of the cyclic acetal. Evidence for the non-limiting mechanism is indicated by analysis of the by-products II-V of the oxidation/hydrolysis/triphosphorylation process shown in the scheme below:

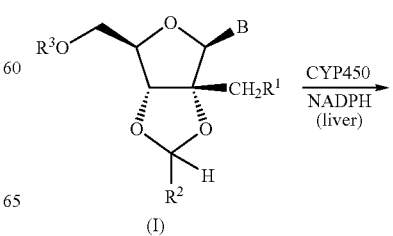

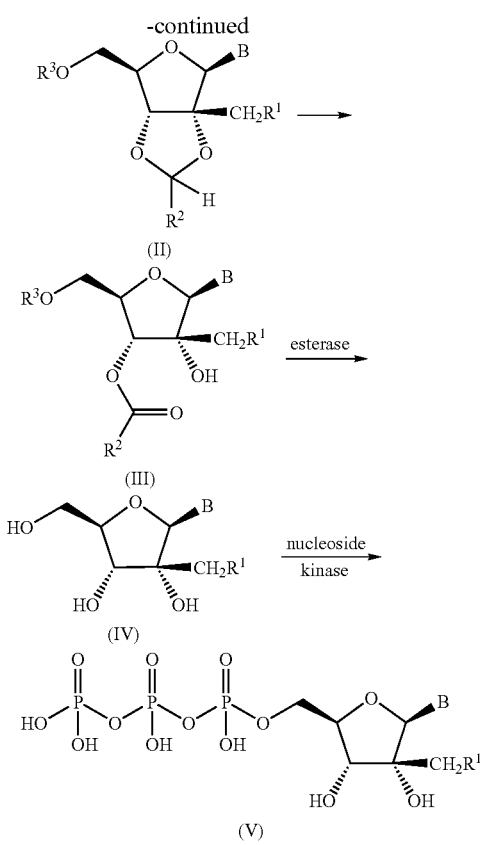

Throughout the instant application, the following terms have the indicated meanings:

"Alkyl", as well as other groups having the prefix "alk", such as alkoxy and alkylthio, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkenyl" shall mean straight or branched chain alkenes of two to six total carbon atoms, or any number within this range (e.g., ethenyl, propenyl, butenyl, pentenyl, etc.).

The term "alkynyl" shall mean straight or branched chain alkynes of two to six total carbon atoms, or any number within this range (e.g., ethynyl, propynyl, butynyl, pentynyl, etc.).

The term "alkoxy" refers to straight or branched chain alkoxides of the number of carbon atoms specified (e.g., $C_{1-4}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-4}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-4}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl ($MeSO_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-4}$ alkyloxycarbonyl), or any number within this range [i.e., methyloxycarbonyl (MeOCO—), ethyloxycarbonyl, or butyloxycarbonyl].

The term "alkylcarbonyl" refers to straight or branched chain alkylacyl group of the number of carbon atoms specified (e.g., $C_{1-4}$ alkylcarbonyl), or any number within this range [i.e., methylcarbonyl (MeCO—), ethylcarbonyl, or butylcarbonyl].

The term "aryl" refers to a mono- or polycyclic aromatic ring system containing carbon ring atoms. The preferred aryls are monocyclic or bicyclic 6-10 membered aromatic ring systems. Phenyl, 1-naphthyl, and 2-naphthyl are preferred aryls. The most preferred aryl is phenyl.

The term "arylcarbonyl" refers to phenylcarbonyl [PhC(=O)—] and naphthylcarbonyl [Naph(C=O)].

The term "aryloxycarbonyl" refers to phenyloxycarbonyl [PhOC(=O)—] and naphthyloxycarbonyl [NaphO(C=O)—].

The term "heteroaryl" refers to an aromatic or partially aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-(1H)-pyridinyl (2-hydroxypyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-α]pyridinyl, [1,2,4-triazolo][4,3-α]pyridinyl, pyrazolo[1,5-α]pyridinyl, [1,2,4-triazolo][1,5-α]pyridinyl, 2-oxo-1,3-benzoxazolyl, 4-oxo-3H-quinazolinyl, 3-oxo-[1,2,4]-triazolo[4,3-α]-2H-pyridinyl, 5-oxo-[1,2,4]-4H-oxadiazolyl, 2-oxo-[1,3,4]-3H-oxadiazolyl, 2-oxo-1,3-dihydro-2H-imidazolyl, 3-oxo-2,4-dihydro-3H-1,2,4-triazolyl, and the like. For heterocyclyl and heteroaryl groups, rings and ring systems containing from 3-15 atoms are included, forming 1-3 rings.

The term "heteroarylcarbonyl" refers to a heteroarylC(=O)— residue wherein the heteroaryl moiety is as defined under "heteroaryl" above.

The term "heteroaryloxycarbonyl" refers to a heteroarylOC(=O)— residue wherein the heteroaryl moiety is as defined under "heteroaryl" above.

The term "halogen" is intended to include the halogen atoms fluorine, chlorine, bromine and iodine.

The term "phosphoryl" refers to —P(O)(OH)$_2$.

The term "diphosphoryl" refers to the radical having the structure:

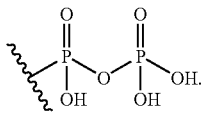

The term "triphosphoryl" refers to the radical having the structure:

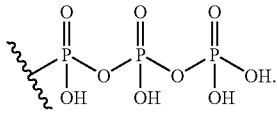

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally.

When $R^{11}$ in the amino acyl residue embodiment of $R^3$ is other than hydrogen in the formula

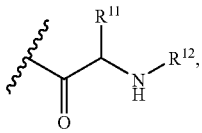

the amino acyl residue contains an asymmetric center and is intended to include the individual R- and S-stereoisomers as well as RS-diastereoisomeric mixtures.

In one embodiment of the compounds of the present invention wherein $R^3$ is a residue of the structural formula:

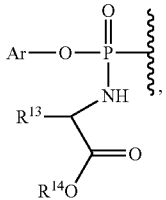

Ar is unsubstituted phenyl.

In a second embodiment of the compounds of the present invention, $R^{13}$ is selected from the group consisting of hydrogen, methyl, ethyl, n-propyl, isopropyl, isobutyl, 2-methyl-1-propyl, hydroxymethyl, mercaptomethyl, carboxymethyl, carbamoylmethyl, 1-hydroxyethyl, 2-carboxyethyl, 2-carbamoylethyl, 2-methylthioethyl, 4-amino-1-butyl, 3-amino-1-propyl, 3-guanidino-1-propyl, 1H-imidazol-4-ylmethyl, phenyl, 4-hydroxybenzyl, and 1H-indol-3-ylmethyl. In a class of this embodiment, $R^{13}$ is methyl or benzyl.

In a third embodiment of the compounds of the present invention, $R^{14}$ is $C_{1-6}$ alkyl, cyclohexyl, phenyl or benzyl. In a class of this embodiment, $R^{14}$ is methyl.

In a fourth embodiment of the compounds of the present invention, $R^3$ is a residue of the structural formula below having the indicated configuration at the stereogenic carbon center to which $R^{13}$ is attached:

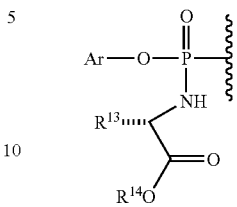

In a class of this fourth embodiment of the compounds of the present invention, Ar is unsubstituted phenyl, $R^{13}$ is methyl or benzyl, and $R^{14}$ is methyl.

The term "composition", as in "pharmaceutical composition," is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The terms "administration of" and "administering a" compound should be understood to mean providing a compound of the invention or a prodrug of a compound of the invention to the individual in need.

Another aspect of the present invention is concerned with a method of inhibiting HCV NS5B polymerase, inhibiting HCV replication, or treating HCV infection with a compound of the present invention in combination with one or more agents useful for treating HCV infection. Such agents active against HCV include, but are not limited to, ribavirin, levovirin, viramidine, thymosin alpha-1, interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffmann-LaRoche, Nutley, N.J.), pegylated interferon-α2a (Pegasys™), interferon-α2b (such as Intron-A interferon available from Schering Corp., Kenilworth, N.J.), pegylated interferon-α2b (PegIntron™), a recombinant consensus interferon (such as interferon alphacon-1), and a purified interferon-α product. Amgen's recombinant consensus interferon has the brand name Infergen®. Levovirin is the L-enantiomer of ribavirin which has shown immunomodulatory activity similar to ribavirin. Viramidine represents an analog of ribavirin disclosed in WO 01/60379 (assigned to ICN Pharmaceuticals). In accordance with this method of the present invention, the individual components of the combination can be administered separately at different times during the course of therapy or concurrently in divided or single combination forms. The instant invention is therefore to be understood as embracing all such regimes of simultaneous or alternating treatment, and the term "administering" is to be interpreted accordingly. It will be understood that the scope of combinations of the compounds of this invention with other agents useful for treating HCV infection includes in principle any combination with any pharmaceutical composition for treating HCV infection. When a compound of the present invention or a pharmaceutically acceptable salt thereof is used in combination with a second therapeutic agent active against HCV, the dose of each compound may be either the same as or different from the dose when the compound is used alone.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in WO 98/22496, WO 98/46630, WO 99/07733, WO 99/07734, WO 99/38888, WO 99/50230, WO 99/64442, WO 00/09543, WO 00/59929, GB-2337262, WO 02/48116, WO 02/48172, WO 05/037214, and U.S. Pat. No. 6,323,180. HCV NS3 protease as a target for the development of inhibitors of HCV replication and for the treatment of HCV infection is discussed in B. W. Dymock, "Emerging therapies for hepatitis C virus infection," *Emerging Drugs*, 6: 13-42 (2001). Specific HCV NS3 protease inhibitors combinable with the compounds of the present invention include BILN2061, VX950, SCH6, and SCH7.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497, which is disclosed in WO 97/41211 and WO 01/00622 (assigned to Vertex); another IMPDH inhibitor, such as that disclosed in WO 00/25780 (assigned to Bristol-Myers Squibb); or mycophenolate mofetil [see A. C. Allison and E. M. Eugui, *Agents Action*, 44 (Suppl.): 165 (1993)].

For the treatment of HCV infection, the compounds of the present invention may also be administered in combination with the antiviral agent amantadine (1-aminoadamantane) [for a comprehensive description of this agent, see J. Kirschbaum, *Anal. Profiles Drug Subs.* 12: 1-36 (1983)].

The compounds of the present invention may also be combined for the treatment of HCV infection with antiviral 2'-C-branched ribonucleosides disclosed in R. E. Harry-O'kuru, et al., *J. Org. Chem.*, 62: 1754-1759 (1997); M. S. Wolfe, et al., *Tetrahedron Lett.*, 36: 7611-7614 (1995); U.S. Pat. No. 3,480, 613 (Nov. 25, 1969); U.S. Pat. No. 6,777,395 (Aug. 17, 2004); U.S. Pat. No. 6,914,054 (Jul. 5, 2005); International Publication Numbers WO 01/90121 (29 Nov. 2001); WO 01/92282 (6 Dec. 2001); WO 02/32920 (25 Apr. 2002); WO 02/057287 (25 Jul. 2002); WO 02/057425 (25 Jul. 2002); WO 04/002422 (8 Jan. 2004); WO 04/002999 (8 Jan. 2004); WO 04/003000 (8 Jan. 2004); WO 04/002422 (8 Jan. 2004); US Patent Application Publications 2005/0107312; US 2005/0090463; US 2004/0147464; and US 2004/0063658; the contents of each of which are incorporated by reference in their entirety. Such 2'-C-branched ribonucleosides include, but are not limited to, 2'-C-methylcytidine, 2'-fluoro-2'-C-methylcytidine 2'-C-methyluridine, 2'-C-methyladenosine, 2'-C-methylguanosine, and 9-(2-C-methyl-β-D-ribofuranosyl)-2,6-diaminopurine; the corresponding amino acid esters of the furanose C-2', C-3', and C-5' hydroxyls (such as 3'-O-(L-valyl)-2'-C-methylcytidine dihydrochloride, also referred to as valopicitabine dihydrochloride or NM-283 and 3'-O-(L-valyl)-2'-fluoro-2'-C-methylcytidine), and the corresponding optionally substituted cyclic 1,3-propanediol esters of their 5'-phosphate derivatives.

The compounds of the present invention may also be combined for the treatment of HCV infection with other nucleosides having anti-HCV properties, such as those disclosed in U.S. Pat. No. 6,864,244 (Mar. 8, 2005); WO 02/51425 (4 Jul. 2002), assigned to Mitsubishi Pharma Corp.; WO 01/79246, WO 02/32920, and WO 02/48165 (20 Jun. 2002), assigned to Pharmasset, Ltd.; WO 01/68663 (20 Sep. 2001), assigned to ICN Pharmaceuticals; WO 99/43691 (2 Sep. 1999); WO 02/18404 (7 Mar. 2002), assigned to Hoffmann-LaRoche; U.S. 2002/0019363 (14 Feb. 2002); WO 02/100415 (19 Dec. 2002); WO 03/026589 (3 Apr. 2003); WO 03/026675 (3 Apr. 2003); WO 03/093290 (13 Nov. 2003): US 2003/0236216 (25 Dec. 2003); US 2004/0006007 (8 Jan. 2004); WO 04/011478 (5 Feb. 2004); WO 04/013300 (12 Feb. 2004); US 2004/0063658 (1 Apr. 2004); and WO 04/028481 (8 Apr. 2004).

In one embodiment, nucleoside HCV NS5B polymerase inhibitors that are used in combination with the ribonucleoside 2',3'-cyclic acetals of the present invention are selected from the following compounds: 4'-azido-cytidine; 4-amino-7-(2-C-methyl-β-D-ribofuranosyl)-7H-pyrrolo[2,3-d]pyrimidine; 4-amino-7-(2-C-hydroxymethyl-β-D-ribofuranosyl)-7H-pyrrolo[2,3-d]pyrimidine; 4-amino -7-(2-C-fluoromethyl-β-D-ribofuranosyl)-7H-pyrrolo[2,3-d]pyrimidine; 4-amino-5-fluoro-7-(2-C-methyl -β-D-ribofuranosyl)-7H-pyrrolo[2,3-d]pyrimidine; 2-amino-7-(2-C-methyl-β-D-ribofuranosyl)-7H -pyrrolo[2,3-d]pyrimidin-4(3H)-one; 4-amino-7-(2-C,2-O-dimethyl-β-D-ribofuranosyl)-7H-pyrrolo[2,3-d]pyrimidine; and pharmaceutically acceptable salts and prodrugs thereof.

The compounds of the present invention may also be combined for the treatment of HCV infection with non-nucleoside inhibitors of HCV polymerase such as those disclosed in WO 01/77091 (18 Oct. 2001), assigned to Tularik, Inc.; WO 01/47883 (5 Jul. 2001), assigned to Japan Tobacco, Inc.; WO 02/04425 (17 Jan. 2002), assigned to Boehringer Ingelheim; WO 02/06246 (24 Jan. 2002), assigned to Istituto di Ricerche di Biologia Moleculare P. Angeletti S. P. A.; WO 02/20497 (3 Mar. 2002); WO 2005/016927 (in particular JTK003), assigned to Japan Tobacco, Inc.; the contents of each of which are incorporated herein by reference in their entirety; and HCV-796 (Viropharma Inc.).

In one embodiment, non-nucleoside HCV NS5B polymerase inhibitors that can be combined with the ribonucleoside 2',3'-cyclic acetals of the present invention are selected from the following compounds:
14-cyclohexyl-6-[2-(dimethylamino)ethyl]-7-oxo-5,6,7,8-tetrahydroindolo[2,1-a][2,5]benzodiazocine-11-carboxylic acid; 14-cyclohexyl-6-(2-morpholin4-ylethyl)-5,6,7,8-tetrahydroindolo[2,1-a][2,5]benzodiazocine-11-carboxylic acid; 14-cyclohexyl-6-[2-(dimethylamino)ethyl]-3-methoxy-5,6,7,8-tetrahydroindolo[2,1-α][2,5]benzodiazocine-11-carboxylic acid; 14-cyclohexyl-3-methoxy-6-methyl -5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl]amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 14-cyclohexyl-N-[(dimethylamino)sulfonyl]-3-methoxy-6-methyl-5,6,7,8-tetrahydroindolo[2,1-α][2,5]benzodiazocine-11-carboxamide; 3-chloro-14-cyclohexyl- 6-[2-(dimethylamino)ethyl]-7-oxo-5,6,7,8-tetrahydroindolo[2,1-a][2,5]benzodiazocine 11-carboxylic acid; N'-(11-carboxy-14-cyclohexyl-7,8-dihydro-6H-indolo[1,2-e][1,5]benzoxazocin-7-yl)-N,N-dimethylethane-1,2-diaminium bis(trifluoroacetate); 14-cyclohexyl-7,8-dihydro-6H-indolo[1,2-e][1,5]benzoxazocine-11-carboxylic acid; 14-cyclohexyl-6-methyl-7-oxo-5,6,7,8-tetrahydroindolo[2,1-α][2,5]benzodiazocine-11-carboxylic acid; 14-cyclohexyl-3-methoxy-6-methyl-7-oxo-5,6,7,8-tetrahydroindolo[2,1-a][2,5] benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamnino)propyl]-7-oxo-5,6,7,8-tetrahydroindolo[2,1-a][2,5] benzodiazocine-11-carboxylic acid; 14-cyclohexyl-7-oxo-6-(2-piperidin-1-ylethyl)-5,6,7,8-tetrahydroindolo[2,1-a][2,5]benzodiazocine-11- carboxylic acid; 14-cyclohexyl-6-(2-morpholin-4-ylethyl)-7-oxo-5,6,7,8-tetrahydroindolo[2,1-a][2,5]benzodiazocine-11-carboxylic acid; 14-cyclohexyl-6-[2-(diethylamino)ethyl]-7-oxo-5,6,7,8-tetrahydroindolo[2,1-α][2,5]benzodiazocine-11-carboxylic acid; 14-cyclohexyl-6-(1-methylpiperidin-4-yl)-7-oxo-5,6,7,8-tetrahydroindolo[2,1-α][2,5]benzodiazocine-11-carboxylic acid; 14-cyclohexyl-N-[(dimethylamino)sulfonyl]-7-oxo-6-(2-piperidin-1-ylethyl)-5,6,7,8-tetrahydroindolo[2,1-a][2,5] benzodiazocine-11-carboxamide; 14-cyclohexyl -6-[2-dimethylamino)ethyl]-N-[(dimethylamino)sulfonyl]-7-oxo-5,6,7,8-tetrahydroindolo[2,1-α][2,5]benzodiazocine-11-carboxamide; 14-cyclopentyl -6-[2-(dimethylamino)ethyl]-7-oxo-5,6,7,8-tetrahydroindolo[2,1-α][2,5] benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy -5,6,7,8-tetrahydroindolo[2,1-a][2,5]benzodiazocine-11-carboxylic acid; 14-cyclopentyl-6-[2-(dimethylamino)ethyl]-5,6,7,8-tetrahydroindolo[2,1-α][2,5] benzodiazocine-11-carboxylic acid; 14-cyclohexyl-6-[2-(dimethylamino)ethyl]-5,6,7,8-tetrahydroindolo[2,1-α][2,5]benzodiazocine-11-carboxylic acid; 13-cyclohexyl-5-methyl-4,5,6,7-tetrahydrofuro[3',2':6,7][1,4]diazocino[1,8-α]indole-10-carboxylic acid; 15-cyclohexyl-6-[2-(dimethylamino)ethyl]-7-oxo-6,7,8,9-tetrahydro-5H-indolo[2,1-α][2,6]benzodiazonine-12-carboxylic acid; 15-cyclohexyl-8-oxo-6,7,8,9-tetrahydro-5H-indolo[2,1-α][2,5]benzodiazonine-12-carboxylic acid; 13-cyclohexyl-6-oxo-6,7-dihydro-5H-indolo[1,2-d][1,4]benzodiazepine-10-carboxylic acid; and pharmaceutically acceptable salts thereof.

By "pharmaceutically acceptable" is meant that the carrier, diluent, or excipient must be compatible with the other ingredients of the formulation and not deleterious to the recipient thereof.

Also included within the present invention are pharmaceutical compositions comprising the ribonucleoside 2',3'-cyclic acetals and analogs and derivatives thereof of the present invention in association with a pharmaceutically acceptable carrier. Another example of the invention is a pharmaceutical composition made by combining any of the compounds described above and a pharmaceutically acceptable carrier. Another illustration of the invention is a process for making a pharmaceutical composition comprising combining any of the compounds described above and a pharmaceutically acceptable carrier.

Also included within the present invention are pharmaceutical compositions useful for inhibiting RNA-dependent RNA viral polymerase, in particular HCV NS5B RNA polymerase comprising an effective amount of a compound of the present invention and a pharmaceutically acceptable carrier. Pharmaceutical compositions useful for treating RNA-dependent RNA viral infection in particular HCV infection are also encompassed by the present invention as well as a method of inhibiting RNA-dependent RNA viral polymerase in particular HCV NS5B polymerase and a method of treating RNA-dependent viral replication and in particular HCV replication. Additionally, the present invention is directed to a pharmaceutical composition comprising a therapeutically effective amount of a compound of the present invention in combination with a therapeutically effective amount of another agent active against RNA-dependent RNA virus and in particular against HCV. Agents active against HCV include, but are not limited to, ribavirin, levovirin, viramidine, thymosin alpha-1, an inhibitor of HCV NS3 serine protease, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as Roferon interferon available from Hoffmann-LaRoche, Nutley, N.J.), interferon-α2b (such as Intron-A interferon available from Schering Corp., Kenilworth, N.J.), a consensus interferon, and a purified interferon-α product. For a discussion of ribavirin and its activity against HCV, see J. O. Saunders and S. A. Raybuck, "Inosine Monophosphate Dehydrogenase: Consideration of Structure, Kinetics, and Therapeutic Potential," *Ann. Rep. Med. Chem.*, 35: 201-210 (2000).

Another aspect of the present invention provides for the use of the ribonucleoside 2',3'-cyclic acetals and analogs and derivatives thereof of the present invention and their pharmaceutical compositions for the manufacture of a medicament for the inhibition of RNA-dependent RNA viral replication, in particular HCV replication, and/or the treatment of RNA-dependent RNA viral infection, in particular HCV infection. Yet a further aspect of the present invention provides for the fluorinated pyrrolo[2,3-d]pyrimidine nucleoside compounds and derivatives thereof and their pharmaceutical compositions for use as a medicament for the inhibition of RNA-dependent RNA viral replication, in particular HCV replication, and/or for the treatment of RNA-dependent RNA viral infection, in particular HCV infection.

The pharmaceutical compositions of the present invention comprise a compound of structural formula I as an active ingredient or a pharmaceutically acceptable salt thereof, and may also contain a pharmaceutically acceptable carrier and optionally other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of structural formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of structural formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of structural formula I are administered orally.

For oral administration to humans, the dosage range is 0.01 to 1000 mg/kg body weight in divided doses. In one embodiment the dosage range is 0.1 to 100 mg/kg body weight in divided doses. In another embodiment the dosage range is 0.5 to 20 mg/kg body weight in divided doses. For oral administration, the compositions are preferably provided in the form of tablets or capsules containing 1.0 to 1000 milligrams of the active ingredient, particularly, 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated.

The effective dosage of active ingredient employed may vary depending on the particular compound employed, the mode of administration, the condition being treated and the severity of the condition being treated. Such dosage may be ascertained readily by a person skilled in the art. This dosage regimen may be adjusted to provide the optimal therapeutic response.

The compounds of the present invention contain one or more asymmetric centers and can thus occur as racemates and racemic mixtures, single enantiomers, diastereomeric mixtures and individual diastereomers. The present invention is meant to comprehend the ribonucleoside 2',3'-cyclic acetals having the β-D stereochemical configuration for the five-membered furanose ring as depicted in the structural formula VI below, that is, ribonucleoside 2',3'-cyclic acetals in which the substituents at C-1 and C-4 of the five-membered furanose ring have the β-stereochemical configuration ("up" orientation as denoted by a bold line).

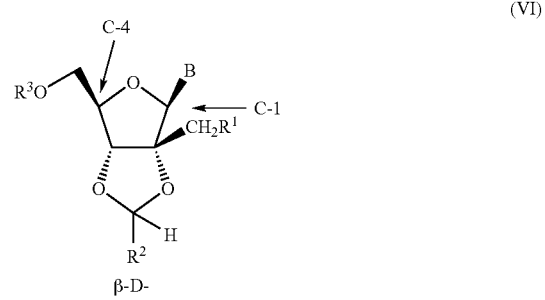
(VI)

In particular, the ribonucleoside 2',3'-cyclic acetals of the present invention contain an asymmetric center at the stereogenic carbon center indicated by an * in the structural formula VII below:

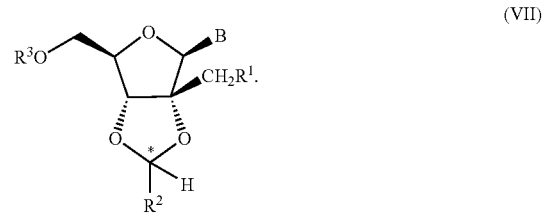
(VII)

The present invention is intended to encompass both diastereomers of structural formulae VIII and IX below, either individually as pure single diastereomers or as variable mixtures of the two diastereomers:

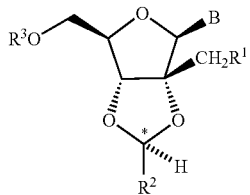

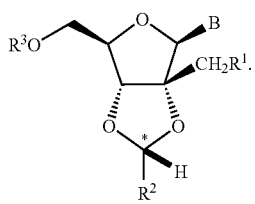

Some of the compounds described herein contain olefinic double bonds, and unless specified otherwise, are meant to include both E and Z geometric isomers.

Some of the compounds described herein may exist as tautomers such as keto-enol and imine-enamine tautomers. The individual tautomers as well as mixtures thereof are encompassed with compounds of structural formula I. Example of keto-enol and imine-enamine tautomers which are intended to be encompassed within the compounds of the present invention are illustrated below:

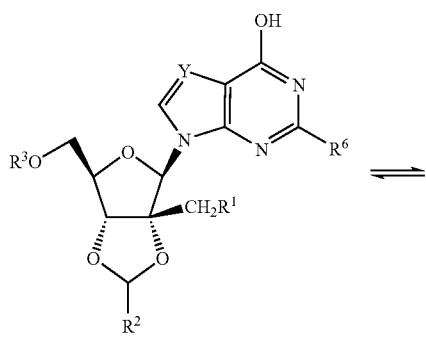

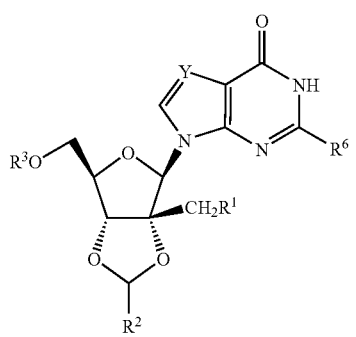

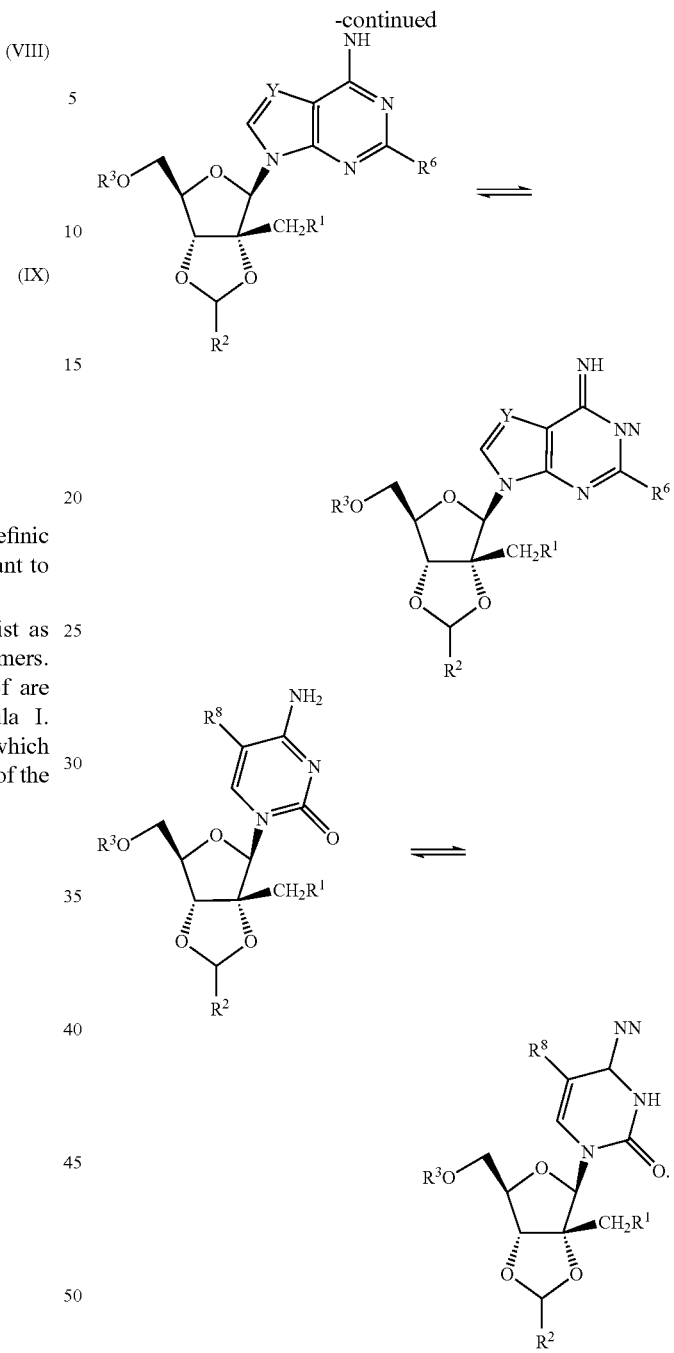

Compounds of structural formula I may be separated into their individual diastereoisomers by, for example, fractional crystallization from a suitable solvent, for example from methanol or ethyl acetate or a mixture thereof, or via chiral chromatography using an optically active stationary phase.

Alternatively, any stereoisomer of a compound of the structural formula I may be obtained by stereospecific synthesis using optically pure starting materials or reagents of known configuration.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH), phosphoric acid [—OP(O)(OH)$_2$], or alcohol group being present in the compounds of the present invention, pharmaceutically acceptable prodrug esters of carboxylic acid derivatives, such as methyl, ethyl, or pivaloyloxymethyl esters; pharmaceutically acceptable prodrug esters of 5'-phosphoric acid derivatives (including 5'-monophosphate, 5'-diphosphate, and 5'-triphosphate) of the ribonucleoside 2',3'-cyclic acetals; or prodrug acyl derivatives of the ribose C-5 hydroxyl, such as O-acetate, O-maleate, and O-aminoacyl, can be employed. Included are those esters and acyl groups known in the art for modifying the bioavailability, tissue distribution, solubility, and hydrolysis characteristics for use as sustained-release or prodrug formulations. The contemplated derivatives are readily convertible in vivo into the required compound. Thus, in the methods of treatment of the present invention, the terms "administering" and "administration" is meant to encompass the treatment of the viral infections described with a compound specifically disclosed or with a compound which may not be specifically disclosed, but which converts to the specified compound in vivo after administration to the mammal, including a human patient. Conventional procedures for the selection and preparation of suitable prodrug derivatives are described, for example, in "Design of Prodrugs," ed. H. Bundgaard, Elsevier, 1985, which is incorporated by reference herein in its entirety.

Preparation of the Compounds of the Invention

The ribonucleoside 2',3'-cyclic acetals of the present invention can be prepared following synthetic methodologies well-established in the practice of nucleoside chemistry. Synthetic methodologies for the preparation of cyclic acetals of 1,2-diols are also described in "Protective Groups in Organic Synthesis," T. W. Greene and P. G. M. Wuts, eds., 2$^{nd}$ Edition, pp. 118-135, 1991.

A typical method is depicted in Scheme 1. According to this method, a ribonucleoside 1a is reacted with a dimethyl acetal of formula 1b in an appropriate protic or aprotic organic solvent, such as methanol, ethanol, THF, DMF, DMSO, dioxane, chloroform, and dichloromethane, in the presence of a suitable acid catalyst, such as p-toluenesulfonic acid and tetrafluoroboric acid.

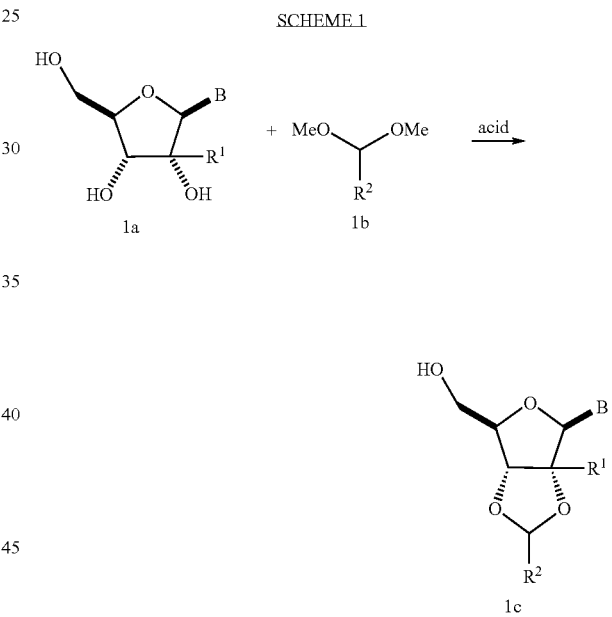

Depending on the conditions applied, the ribonucleoside 2',3'-cyclic acetal 1c can be obtained in a form of a single diastereoisisomer or as a mixture of diastereomers at the stereogenic acetal carbon atom. Each pure diastereomer can also be obtained by fractional crystallization or by chromatographic methods.

The nucleoside acetals of the present invention can also be prepared by reacting a ribonucleoside of structural formula 1a with an aldehyde of formula 2a in a suitable organic solvent, such as THF, benzene, and N,N-dimethylformamide (DMF) in the presence of either a Lewis acid catalyst, such as zinc chloride and boron trifluoride etherate, or a protic acid, such as p-toluenesulfonic acid, optionally in the presence of a trialkyl orthoformate, such as trimethyl and triethyl orthoformate, as depicted in Scheme 2. The reactions are carried out from ice temperature to refluxing temperature of the reaction solvent.

SCHEME 2

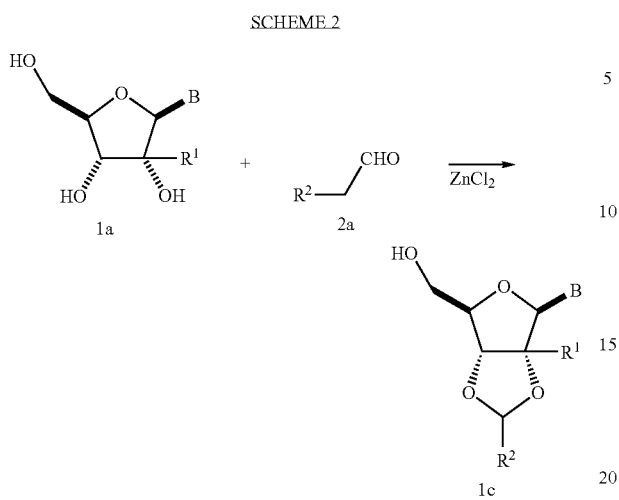

The Examples below provide illustrations of the conditions used for the preparation of the compounds of the present invention. These Examples are not intended to be limitations on the scope of the instant invention in any way, and they should not be so construed. Those skilled in the art of nucleoside and nucleotide synthesis will readily appreciate that known variations of the conditions and processes of the following preparative procedures can be used to prepare these and other compounds of the present invention. All temperatures are degrees Celsius unless otherwise noted.

EXAMPLE 1

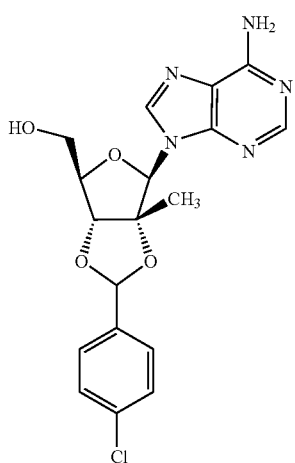

A suspension of 2'-C-methyladenosine [prepared following the conditions described in *J. Med. Chem.*, 41: 1708 (1998)] (6.50 g, 23.1 mmol), zinc(II) chloride (15.8 g, 115.5 mmol) and p-chlorobenzaldehyde (32.5 g, 231 mmol) in dry tetrahydrofuran (20 mL) was stirred at 60° C. for 12 h. The reaction was quenched with aqueous solution of sodium hydroxide (150 mL, 2N) and the crude product was extracted with chloroform (2×250 mL). The combined organic extracts were dried with anhydrous magnesium sulfate and the solvent was removed in vacuo. The residue was further purified by column chromatography on silica gel using 9:1 dichloromethane/methanol as eluant to afford a mixture of the two diastereomeric (5:1 ratio) products as a white powder. $^1$H NMR (500 MHz, dimethylsulphoxide-$d_6$): Major isomer: δ=8.40 (s, 1H), 8.15 (s, 1H), 7.65 (d, J=8.24, 2H), 7.54 (d, J=8.23, 2H), 7.36 (brs, 2H), 6.40 (s, 1H), 6.18 (s, 1H), 5.42 (t, J=5.49, 1H), 4.71 (d, J=3.43, 1H), 4.28 (q, J=3.54, 1H), 3.75 (m, 1H), 1.19 (s, 3H). Minor isomer: δ=8.40 (s, 1H), 8.15 (s, 1H), 7.54 (d, J=8.23, 2H), 7.49 (d, J=8.46, 2H), 6.40 (s, 1H), 6.33 (s, 1H), 5.39 (t, J=5.72, 1H), 4.67 (d, J=4.58, 1H), 4.31 (q, J=3.89, 1H), 3.75 (m, 1H), 1.12 (s, 3H). $^{13}$C NMR (500 MHz, dimethylsulphoxide-$d_6$): major isomer: δ=156.1, 152.8, 148.9, 139.1, 135.4, 134.3, 129.0, 128.6, 128.5, 118.8, 104.8, 102.3, 91.3, 90.8, 86.4, 84.4, 61.3, 16.9. Mass spectrum: for $C_{18}H_{18}N_5O_4$ calculated 403.10, found 404.3 $[M+H]^+$.

EXAMPLE 2

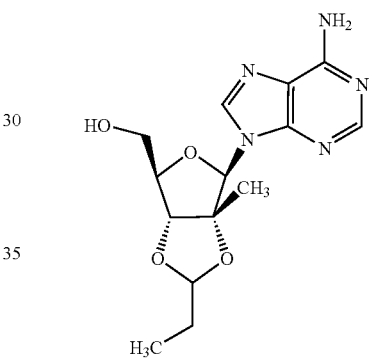

A suspension of 2'-C-methyladenosine (140 mg, 0.5 mmol), p-toluenesulfonic acid monohydrate (144 mg, 0.75 mmol) and propionaldehyde dimethylacetal (417 mg, 4 mmol) in dry N,N-dimethylformamide (4 mL) was stirred at 25° C. for 12 h. Additional propionaldehyde dimethylacetal (417 mg, 4 mmol) and p-toluenesulfonic acid monohydrate (432 mg, 2.25 mmol) were added and the mixture was heated to 50° C. for 3 h. The reaction was quenched with an aqueous solution of saturated sodium bicarbonate (5 mL) and the crude product was extracted with tert-butyl methyl ether (4×20 mL). The combined organic extracts were dried with anhydrous magnesium sulfate and the solvent was removed in vacuo. The residue was further purified by mass directed HPLC chromatography (reversed phase, Waters Sunfire Prep C18 ODB 10 μm [30×100 mm], acetonitrile [0.1% TFA]/ water [0.1% TFA] gradient) to afford the product as a clear oil. $^1$H NMR (500 MHz, dimethylsulphoxide-$d_6$): δ=8.55 (s, 1H), 8.35 (s, 1H), 6.24 (s, 1H), 5.19 (t, J=4.46, 1H), 4.51 (d, J=3.20, 1H), 4.20 (q, J=3.51, 1H), 3.72 (dd, J'=3.78, J''=12.13, 2H), 1.74 (m, 2H), 1.08 (s, 3H), 0.97 (t, J=7.55, 3H). $^3$C NMR (500 MHz, methanol-$d_4$): δ=147.4, 143.2, 109.5, 94.4, 91.7, 87.8, 86.8, 62.8, 28.0, 17.4, 8.1. Mass spectrum: for $C_{14}H_{19}N_5O_4$ calculated 321.33, found 322.4 $[M+H]^+$.

EXAMPLE 3

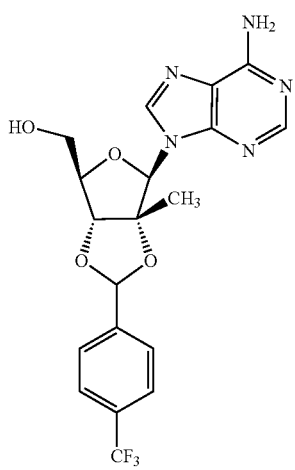

A suspension of 2'-C-methyladenosine (240 mg, 0.85 mmol), zinc(II) chloride (581 mg, 4.3 mmol) and p-trifluoromethylbenzaldehyde (2 mL) was stirred at 60° C. for 12 h. The aldehyde was removed via distillation. The residue was purified by mass directed HPLC chromatography (reversed phase, Waters Sunfire Prep C18 ODB 10 μm [30×100 mm], acetonitrile [0.1% TFA]/water [0.1% TFA] gradient) to afford the pure product (white powder) as a mixture of two diastereomers (4:1 ratio). $^1$H NMR (500 MHz, methanol-d$_4$): Major isomer: δ=8.68 (s, 1H), 8.38 (s, 1H), 7.84 (d, J=8.23, 2H), 7.77 (d, J=8.24, 2H), 6.54 (s, 1H), 6.32 (s, 1H), 4.80 (d, J=2.97, 1H), 4.44 (q, J=3.00, 1H), 3.96 (dd, J'=3.43, J"=12.36, 1H), 3.88 (dd, J'=3.43, J"=12.35, 1H), 1.28 (s, 3H). Minor Isomer: δ=8.68 (s, 1H), 8.38 (s, 1H), 7.73 (m, 4H), 6.56 (s, 1H), 6.39 (s, 1H), 4.75 (d, J=4.57, 1H), 4.44 (q, J=3.00, 1H), 4.04 (dd, J'=2.75, J"=12.36, 1H), 3.92 (dd, J'=3.21, J"=12.36, 1H), 1.20 (s, 3H). $^{13}$C NMR (500 MHz, methanol-d$_4$): Major isomer: δ=152.5, 149.8, 146.3, 146.2, 143.5, 128.7, 126.5, 126.4, 107.0, 104.4, 94.2, 93.1, 92.5, 88.6, 86.4, 62.8, 62.6, 17.4. Mass spectrum: for $C_{14}H_{19}N_5O_4$ calculated 437.37, found 438.34$[M+H]^+$.

The following additional 2',3'-cyclic acetals of 2'-C-methyladenosine were prepared following the procedures described above.

| Example | $R^2$ | Mass spectrum [M + 1] |
|---|---|---|
| 4 | phenyl | 370.2 |
| 5 | 4-methoxyphenyl | 400.1 |
| 6 | 3-methoxyphenyl | 400.1 |
| 7 | 2-methoxyphenyl | 400.1 |
| 8 | 4-methylphenyl | 384.2 |
| 9 | 4-isopropylphenyl | 412.2 |
| 10 | 3-chlorophenyl | 404.3 |
| 11 | 2-chlorophenyl | 404.2 |
| 12 | n-hexyl | 378.3 |
| 13 | isopropyl | 336.4 |
| 14 | t-butyl | 350.3 |
| 15 | ![sec-butyl] | 364.5 |
| 16 | isobutyl | 350.37 |
| 17 | 3-thionyl | 376.5 |
| 18 | 2-(phenyl)phenyl | 446.5 |
| 19 | 2-methylphenyl | 384.5 |
| 20 | 2-fluorophenyl | 388.5 |
| 21 | 1-naphthyl | 420.20 |
| 22 | 2-(trifluoromethoxy)-phenyl | 436.32 |
| 23 | 2-(methylthio)phenyl | 416.4 |

5'-Ester derivatives of the ribonucleoside 2',3'-cyclic acetals of the present invention were prepared as shown in Scheme 3 and described in Example 24.

SCHEME 3

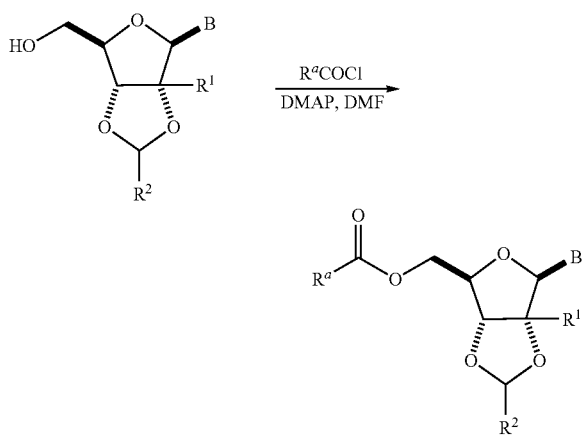

EXAMPLE 24

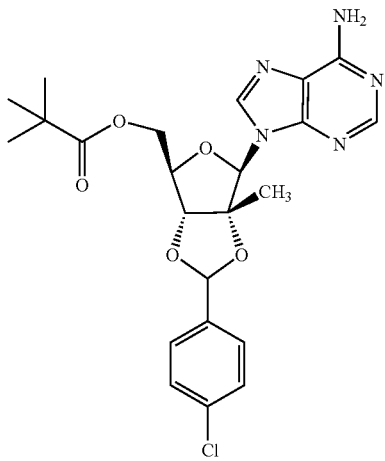

The compound of Example 1 (70 mg, 0.17 mmol), pivaloyl chloride (22 μL, 0.17 mmol), 4-dimethylaminopyridine (DMAP, 10 mg) were dissolved in dry N,N-dimethylformamide (1 mL) and stirred at 25° C. for 12 h. The solution was concentrated in vacuo and purified by column chromatography on silica gel using ethyl acetate as eluant to yield the product as a mixture of two diastereomers (3:1 ratio) in the form of a white powder. $^1$H NMR (500 MHz, methanol-$d_4$): Major isomer: δ=8.22 (m, 2H), 7.62 (d, J=8.46, 2H), 7.45 (d, J=8.24, 2H), 6.44 (s, 1H), 6.21 (s, 1H), 4.77 (d, J=4.35, 1H), 4.53 (m, 1H), 4.46 (d, J=5.49, 1H), 4.42 (dd, J'=1.60, J"=4.57, 1H), 1.28 (m, 3H), 1.23 (s, 3H), 1.20 (m, 6H). Minor Isomer: δ=8.22 (m, 2H), 7.54 (d, J=8.47, 2H), 7.41 (d, J=8.47, 2H), 6.43 (s, 1H), 6.33 (s, 1H), 4.69 (d, J=4.58, 1H), 4.51 (m, 1H), 4.49 (d, J=4.57, 1H), 4.44 (m, 1H), 1.28 (m, 3H), 1.20 (m, 3H), 1.17 (m, 6H). $^{13}$C NMR (500 MHz, methanol-$d_4$): Major isomer: δ=179.6, 157.4, 154.2, 140.8, 136.9, 136.5, 129.7, 129.6, 129.5, 107.4, 104.7, 92.3, 92.0, 87.9, 83.2, 80.6, 65.0, 39.8, 27.8, 27.6, 27.5, 19.9, 17.5. Mass spectrum: for $C_{14}H_{19}N_5O_4$ calculated 487.16, found 488.1[M+H]$^+$.

The following additional 5'-ester derivatives of the ribonucleoside 2',3'-cyclic acetals of the present invention were prepared following the procedure described for Example 24.

| Example | R$^2$ | R$^3$ | Mass spectrum [M + 1] |
|---|---|---|---|
| 25 | 4-chlorophenyl | benzoyl | 508.3 |
| 26 | 4-chlorophenyl | N-Boc-valyl | 603.2 |
| 27 | 4-chlorophenyl | 4-chlorobenzoyl | 542.3 |
| 28 | 4-chlorophenyl | isovaleryl | 488.2 |

-continued
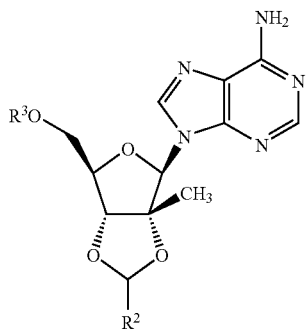
| Example | R² | R³ | Mass spectrum [M + 1] |
|---|---|---|---|
| 29 | 4-chlorophenyl | isopropyl-CH(NH₂)-C(=O)- | 503.4 |
| 30 | 4-chlorophenyl | H₃C-C(=O)- | 446.1 |
| 31 | 4-chlorophenyl | isopropyl-C(=O)- | 474.2 |
| 32 | 4-chlorophenyl | n-pentyl-C(=O)- | 502.1 |
| 33 | 4-chlorophenyl | ethyl-C(=O)- | 460.32 |
| 34 | 4-chlorophenyl | n-heptyl-C(=O)- | 530.4 |
| 35 | 4-chlorophenyl | cyclopropyl-C(=O)- | 472.3 |
| 36 | 4-chlorophenyl | cyclobutyl-C(=O)- | 486.1 |

-continued

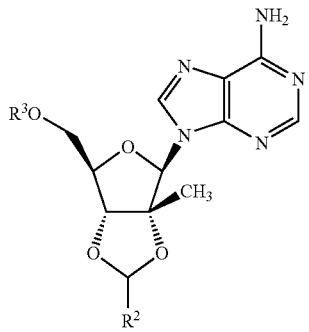

| Example | R² | R³ | Mass spectrum [M + 1] |
|---|---|---|---|
| 37 | 4-chlorophenyl | (3-pyridyl-C(O)-CH₂-) | 509.3 |
| 38 | 4-chlorophenyl | ((CH₃)₂N-CH₂-C(O)-) | 489.2 |

EXAMPLE 39

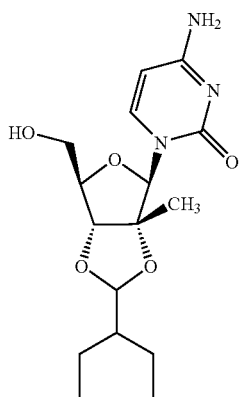

A solution of 2'-C-methylcytidine [prepared following the conditions described in *Carbohyd. Res.*, 166: 219-232 (1987)] (64 mg, 0.25 mmol), zinc (II) chloride (170 mg, 1.25 mmol) and 2-ethylbutyraldehyde (1 mL) was stirred at 60° C. for 12 h. The reaction was quenched with an aqueous solution of sodium hydroxide (5 mL, 2N) and the crude product was extracted with 85/15 chloroform/isopropyl alcohol (3×15 mL). The combined organic extracts were dried with anhydrous magnesium sulfate and the solvent was removed in vacuo. The residue was further purified by column chromatography on silica gel using 9:1 dichloromethane/methanol as eluant to give the desired compound as a 3:1 mixture of two diastereomers in a form of a white powder. ¹H NMR (500 MHz, methanol-d₄): major isomer: δ=7.95 (d, J=7.55, 1H), 6.12 (s, 1H), 5.89 (m, 1H), 5.15 (d, J=4.35, 1H), 4.35 (d, J=4.34, 1H), 4.11 (q, J=3.66, 1H), 3.84 (dd, J'=2.92, J''=12.36, 1H), 3.75 (dd, J'=3.66, J''=12.36, 1H), 1.56 (m, 2H), 1.43 (m, 2H), 1.18 (s, 3H), 0.94 (m, 6H). minor isomer: δ=7.91 (d, J=8.01, 1H), 6.10 (s, 1H), 5.89 (m, 1H), 5.23 (d, J=3.89, 1H), 4.32 (d, J=5.26, 1H), 4.07 (m, 1H), 3.90 (dd, J'=2.52, J''=12.13, 1H), 3.78 (m, 1H), 1.56 (m, 2H), 1.43 (m, 2H), 1.14 (s, 3H), 0.94 (m, 6H). ¹³C NMR (500 MHz, methanol-d₄): major isomer: δ=167.6, 158.2, 143.2, 110.4, 95.6, 92.0, 86.8, 86.0, 62.5, 45.8, 22.3, 22.0, 19.7, 17.4, 11.8, 11.7. Mass spectrum: for $C_{19}H_{18}N_5O_4$ calculated 339.39, found 340.31 [M+H]⁺.

The following additional 2',3''-cyclic acetals of 2'-C-methylcytidine were prepared following the procedures described above.

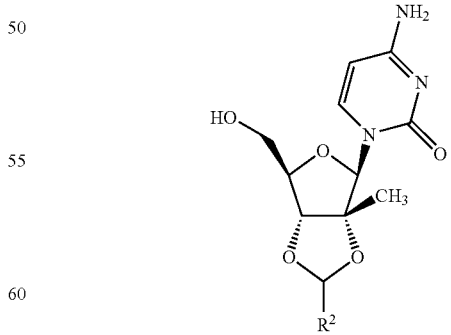

| Example | R² | Mass spectrum [M + 1] |
|---|---|---|
| 40 | phenyl | 346.1 |
| 41 | 4-chlorophenyl | 380.2 |

-continued

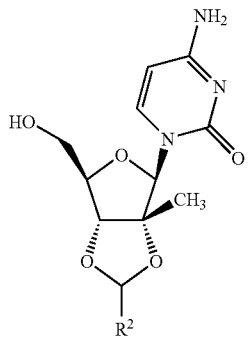

| Example | R² | Mass spectrum [M + 1] |
|---|---|---|
| 42 | n-hexyl | 354.3 |
| 43 | t-butyl | 326.3 |
| 44 | isobutyl | 326.4 |
| 45 | cyclopropyl | 310.2 |

EXAMPLE 46

Nucleoside 5'-Triphosphates

The 5'-triphosphates of structural formula V were prepared according to the general procedures described in *Chem. Rev.* 100: 2047 (2000).

EXAMPLE 47

Purification and Purity Analysis of Nucleoside 5'-Triphosphates

Triphosphates were purified by anion exchange (AX) chromatography using a 30×100 mm Mono Q column (Pharmacia) with a buffer system of 50 mM Tris, pH 8. Elution gradients were typically from 40 mM NaCl to 0.8 M NaCl in two column volumes at 6.5 mL/min. Appropriate fractions from anion exchange chromatography were collected and desalted by reverse-phase (RP) chromatography using a Luna C18 250×21 mm column (Phenomenex) with a flow rate of 10 ml/min. Elution gradients were generally from 1% to 95% methanol in 14 min at a constant concentration of 5 mM triethylammonium acetate (TEAA).

Mass spectra of the purified triphosphates were determined using on-line HPLC mass spectrometry on a Hewlett-Packard (Palo Alto, CA) MSD 1100. A Phenomenex Luna (C18(2)), 150×2 mm, plus 30×2 mm guard column, 3-µm particle size was used for RP HPLC. A 0 to 50% linear gradient (15 min) of acetonitrile in 20 mM TEAA (triethylammonium acetate) pH 7 was performed in series with mass spectral detection in the negative ionization mode. Nitrogen gas and a pneumatic nebulizer were used to generate the electrospray. The mass range of 150-900 was sampled. Molecular masses were determined using the HP Chemstation analysis package.

The purity of the purified triphosphates was determined by analytical RP and AX HPLC. RP HPLC with a Phenomenex Luna or Jupiter column (250×4.6 mm), 5-µm particle size was typically run with a 2-70% acetonitrile gradient in 15 min in 100 mM TEAA, pH 7. AX HPLC was performed on a 1.6×5 mm Mono Q column (Pharmacia). Triphosphates were eluted with a gradient of 0 to 0.4 M NaCl at constant concentration of 50 mM Tris, pH 8. Purity of the triphosphates was generally greater than 80%.

Biological Assays

A. In Vitro Liver Ribonucleoside 2',3'-cyclic Acetal Conversion Screen

An in vitro assay was employed to evaluate conversion of the ribonucleoside 2',3'-cyclic acetals of the present invention to the corresponding ribonucleosides of structural formula IV when incubated with rat dog or human liver S9 homogenates in the presence or absence of NADPH co-factor required by cytochrome P450 mixed function oxidases. Rat liver S9 was prepared by homogenizing approximate 8 gram pieces of fresh liver from male Sprague-Dawley rats (N=2; 3 w/v in EDTA-free buffers to prevent irreversible deactivation of the calcium-dependent esterase-paraoxonase) and centrifugation (10,000 g for 30 min at 4° C.). Protein concentration of the supernatant (S-9) was estimated using the bicinchoninic (BCA) protein assay versus bovine serum albumin (BSA) standards.

Ribonucleoside 2',3'-cyclic acetals of structural formula I at a concentration of 10 µM were incubated with 4 mg/mL rat liver S9 in 100 mM sodium phosphate buffer, pH 7.4 and 1 mM NADPH (w/NADPH regenerating system) for 60 min at 37° C. Control incubations were carried out with 4 mg/mL rat liver S9 (dialyzed to remove residual NADPH) without NADPH or an NADPH regenerating system. Incubations were stopped with the addition of 2 volumes of acetonitrile (with 0.2 v/v % formic acid), vortexed, centrifuged. Supernatant was diluted 10-fold with water and analyzed directly by LC-ESI MS/MS in positive ion selected-reaction monitoring mode. Conversion of the ribonucleoside 2',3'-cyclic acetals to the corresponding ribonucleosides thereof was quantitated versus standards.

B. In Vivo Liver Ribonucleotide Measurements

Ribonucleosides or ribonucleoside 2',3'-cyclic acetals were dosed to rats by oral gavage at a dose equimolar to 5 mg/kg of the comparator nucleosides: 2'-C-methyladenosine and 2'-C-methylcytidine. At specified time points (for example, 30 min, 1 h, 2 h, and 5 h) after dosing, animals were administered isoflurane and abdominal cavity was opened. Samples of portal (about 200 µL) and systemic blood (about 5 mL) were withdrawn directly from the portal vein or inferior vena cava, respectively. While animals were under deep isoflurane anesthesia, 1-2 sections of liver were freeze-clamped in vivo using brass clamps pre-cooled in liquid nitrogen. Frozen liver sections were then stored at −70° C. until analysis. For selected prodrugs, corresponding tritiated radiotracers were dosed and total liver radioactivity levels were measured after combustion on a Packard automated oxidizer followed by liquid scintillation counting (LSC).

Pieces of frozen liver were homogenized on ice in 3 v/w 70/30 methanol/20 mM aqueous EDTA/EGTA (pH 7.0). The addition of EDTA/EGTA was required to chelate magnesium and thus minimize residual adenylate kinase activity which results in equilibration of the mono-, di- and triphosphates. Homogenate was centrifuged and aliquots of supernatant were either dried down and reconstituted in water with direct HPLC-MS/MS-radiochemical profiling/analysis (Method A, below) or further cleaned-up using a solid phase extraction (SPE) method prior to analysis by LC-ESI MS/MS (Method B, below). Using the latter method, liver levels of the corresponding 5'-phosphorylated ribonucleosides were measured directly against standards.

Chromatographic Analysis Method A

Reconsituted liver homogenates were analyzed using a Waters ODS-AQ 120A 4.6×25 cm HPLC column at a flow rate of 1 mL/min (flow split: 200 uL/min to Thermo-Electron Quantum ESI MS source and 800 uL/min to radioflow detector). The following gradient method was used to separate nucleotides, nucleoside prodrugs, nucleoside and prodrug metabolites for radioprofiling work: 0-15 min: 0-15% solvent B; 15-25 min: 15-90% B; 25-27 min: 90-0% B; 27-30 min: 100% A where solvent A=10 mM aqueous ammonium acetate (pH unadjusted) and solvent B=100% acetonitrile.

The identities of nucleotides, nucleosides, and corresponding metabolites were confirmed by LC-MS/MS in positive ion electrospray (ESI) mode.

Chromatographic Analysis Method B

Liver homogenates were cleaned up via solid phase extraction (SPE) using a Phenomenex Strata-X-AW 30 mg weak anion exchange 96-well plate. Post SPE, analytes were separated using a reversed phase chromatographic method and detected on a Sciex API 3000 mass spectrometer. The separation was on an ACE C18 column (0.2×5 cm) using a solvent gradient from 100% A: 10 mM aqueous ammonium acetate +0.1% dimethyl hexylamine to 40% solvent B: 10 mM ammonium acetate +0.1% dimethyl hexylamine in 95/5 acetonitrile/water over a gradient time of 6 min. The flow rate was 0.5 mL/min. Mono-, di- and triphosphate anabolites were ionized in a TurboIonspray source and measured via selected reaction monitoring (SRM) in negative ion mode. Nucleotide standards were spiked into control liver homogenates and were processed identically to samples. Calibration curves were constructed by plotting the peak area ratios (analyte over the internal standard) against the known concentration of each analyte in liver. The concentrations of each analyte in the unknown samples were determined by interpolation from the calibration curves.

Blood was immediately added (1:2) to cold acetonitrile (w/0.2 v/v % formic acid) to inactivate esterases and/or deaminase activity. Ribonucleoside 2',3'-cyclic acetal levels and/or metabolite levels were measured in the supernatants of blood samples obtained in this manner by LC-MS to confirm both the degree of intestinal absorption as well as intestinal degradation/metabolism of each ribonucleoside 2',3'-cyclic acetal. For selected ribonucleoside 2',3'-cyclic acetals, corresponding tritiated radiotracers were prepared and total blood radioactivity levels were measured after combustion on a Packard automated oxidizer followed by liquid scintillation counting (LSC). LC analysis with radiochemical profiling was also performed.

The effectiveness of the 5'-triphosphate derivatives of structural formula V as inhibitors of HCV NS5B RNA-dependent RNA polymerase (RdRp) was measured in the following assay:

Assay for Inhibition of HCV NS5B Polymerase

This assay was used to measure the ability of the 5'-triphosphate derivatives of structural formula V to inhibit the enzymatic activity of the RNA-dependent RNA polymerase (NS5B) of the hepatitis C virus (HCV) on a heteromeric RNA template.

Procedure

Assay Buffer Conditions: (50 µL -total/reaction)
  20 mM Tris, pH 7.5
  50 µM EDTA
  5 mM DTT
  2 mM $MgC_2$
  80 mM KCl
  0.4 U/µL RNAsin (Promega, stock is 40 units/µL)
  0.75 µg t500 (a 500-nt RNA made using T7 runoff transcription with a sequence from the NS2/3 region of the hepatitis C genome)
  1.6 µg purified hepatitis C NS5B (form with 21 amino acids C-terminally truncated)
  1 µM A, C, U, GTP (Nucleoside triphosphate mix)
  [alpha-$^{32}$P]-GTP or [alpha-$^{33}$P]-GTP The ribonucleoside triphosphates were tested at various concentrations up to 100 µM final concentration.

An appropriate volume of reaction buffer was made including enzyme and template t500. Ribonucleoside triphosphates of the present invention were pipetted into the wells of a 96-well plate. A mixture of nucleoside triphosphates (NTP's, nucleoside triphosphate mix), including the radiolabeled GTP, was made and pipetted into the wells of a 96-well plate. The reaction was initiated by addition of the enzyme-template reaction solution and allowed to proceed at room temperature for 1-2 h.

The reaction was quenched by addition of 20 ,µL 0.5M EDTA, pH 8.0. Blank reactions in which the quench solution was added to the NTP's prior to the addition of the reaction buffer were included.

50 µL of the quenched reaction were spotted onto DE81 filter disks (Whatman) and allowed to dry for 30 min. The filters were washed with 0.3 M ammonium formate, pH 8 (150 mL/wash until the cpm in 1 mL wash is less than 100, usually 6 washes). The filters were counted in 5-mL scintillation fluid in a scintillation counter.

The percentage of inhibition was calculated according to the following equation:

% Inhibition=[1−(cpm in test reaction−cpm in blank)/(cpm in control reaction−cpm in blank)]×100.

Representative ribonucleoside triphosphates tested in the HCV NS5B polymerase assay exhibited $IC_{50}$'s less than 50 micromolar.

EXAMPLE OF A PHARMACEUTICAL FORMULATION

As a specific embodiment of an oral composition of a compound of the present invention, 50 mg of the compound of Example 1 is formulated with sufficient finely divided lactose to provide a total amount of 580 to 590 mg to fill a size O hard gelatin capsule.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for severity of the HCV infection. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:

1. A compound of structural formula I having the indicated stereochemical configuration:

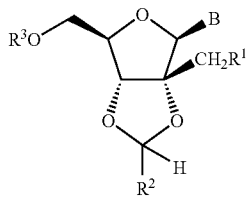

or a pharmaceutically acceptable salt thereof;

wherein B is

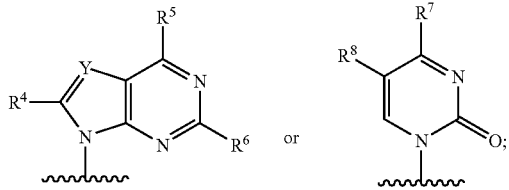

Y is N or $CR^{10}$;

$R^1$ is selected from the group consisting of hydrogen, fluoro, amino, hydroxy, and methoxy;

$R^2$ is selected from the group consisting of $C_{1-12}$ alkyl, $C_{3-8}$ cycloalkyl, aryl, and heteroaryl;

wherein alkyl and cycloalkyl are unsustituted or substituted with one to three substituents independently selected from halogen, hydroxy, carboxy, and $C_{1-4}$ alkoxy; and aryl and heteroaryl are unsubstituted or substituted with one to five substituents independently selected from $R^9$;

$R^3$ is selected from the group consisting of hydrogen, $C_{1-16}$ alkylcarbonyl, $C_{2-18}$ alkenylcarbonyl, $C_{1-10}$ alkyloxycarbonyl, $C_{3-6}$ cycloalkylcarbonyl, $C_{3-6}$ cycloalkyloxycarbonyl, arylcarbonyl, aryloxycarbonyl, heteroarylcarbonyl, heteroaryloxycarbonyl, an amino acyl residue of structural formula:

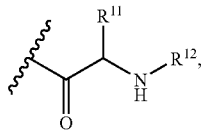

or a residue of structural formula:

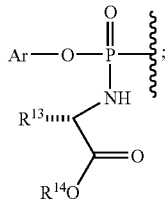

wherein alkylcarbonyl, alkyloxycarbonyl, cycloalkylcarbonyl, and cycloalkyloxycarbonyl are unsubstituted or substituted with one to three substituents independently selected from the group consisting of halogen, hydroxy, carboxy, $C_{1-4}$ alkoxy, amino, $C_{1-4}$ alkylamino, and di($C_{1-4}$ alkyl)amino and wherein arylcarbonyl, aryloxycarbonyl, heteroarylcarbonyl, and heteroaryloxycarbonyl are unsubstituted or substituted with one to five substituents independently selected from $R^9$;

Ar is phenyl unsubstituted or substituted with one to three substituents independently selected from the group consisting of halogen, $C_{1-4}$ alkyl, $C_{1-4}$ alkoxy, $C_{1-4}$ alkylthio, cyano, nitro, amino, carboxy, trifluoromethyl, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl;

$R^4$ is hydrogen, halogen, methyl, azido, cyano, or amino;

$R^5$, $R^6$, and $R^7$ are each independently hydroxy, halogen, amino, $C_{1-4}$ alkylamino, di($C_{1-4}$ alkyl)amino, $C_{3-6}$ cycloalkylamino, or di($C_{3-6}$ cycloalkyl)amino;

$R^8$ is hydrogen, $C_{1-3}$ alkyl, $C_{2-4}$ alkenyl, $C_{2-4}$ alkynyl, $C_{1-4}$ alkylamino, $CF_3$, or halogen;

each $R^9$ is independently selected from the group consisting of halogen, $C_{1-4}$ alkyl, $C_{1-4}$ alkoxy, $C_{1-4}$ alkylthio, $C_{1-4}$ alkylsulfonyl, cyano, nitro, amino, phenyl, carboxy, trifluoromethyl, difluoromethoxy, trifluoromethoxy, $C_{1-4}$ alkylamino, di($C_{1-4}$ alkyl)amino, $C_{1-4}$ alkylcarbonyl, $C_{1-4}$ alkylcarbonyloxy, and $C_{1-4}$ alkyloxycarbonyl;

$R^{10}$ is hydrogen, fluorine, cyano, $C_{1-3}$ alkyl, $NHCONH_2$, $C(=O)NR^{15}R^{15}$, $C(=S)NR^{15}R^{15}$, $C(=O)OR^{15}$, $C(=NH)NH_2$, hydroxy, $C_{1-3}$ alkoxy, amino, $C_{1-4}$ alkylamino, di($C_{1-4}$ alkyl)amino, $C_{2-4}$ alkenyl, or $C_{2-4}$ alkynyl;

$R^{11}$ is hydrogen, $C_{1-5}$ alkyl, or phenyl $C_{0-2}$ alkyl;

$R^{12}$ is hydrogen, $C_{1-4}$ alkyl, $C_{1-4}$ acyl, benzoyl, $C_{1-4}$ alkyloxycarbonyl, phenyl $C_{0-2}$ alkyloxycarbonyl, $C_{1-4}$ alkylaminocarbonyl, phenyl $C_{0-2}$ alkylaminocarbonyl, $C_{1-4}$ alkylsulfonyl, or phenyl $C_{0-2}$ alkylsulfonyl;

$R^{13}$ is hydrogen, $C_{1-5}$ alkyl, phenyl or benzyl;

wherein alkyl is unsubstituted or substituted with one substituent selected from the group consisting of hydroxy, methoxy, amino, carboxy, carbamoyl, guanidino, mercapto, methylthio, 1H-imidazolyl, and 1H-indol-3-yl; and wherein phenyl and benzyl are unsubstituted or substituted with one to two substituents independently selected from the group consisting of halogen, hydroxy, and methoxy;

$R^{14}$ is hydrogen, $C_{1-6}$ alkyl, $C_{3-6}$ cycloalkyl, phenyl, or benzyl;

wherein alkyl and cycloalkyl are unsubstituted or substituted with one to three substituents independently selected from halogen, hydroxy, carboxy, $C_{1-4}$ alkoxy; and wherein phenyl and benzyl are unsubstituted or substituted with one to three substituents independently selected from halogen, hydroxy, cyano, $C_{1-4}$ alkoxy, and trifluoromethyl; and each $R^{15}$ is independently hydrogen or $C_{1-6}$ alkyl.

2. The compound of claim 1 wherein B is:

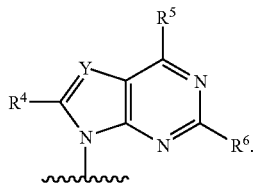

3. The compound of claim 2 wherein Y is N.

4. The compound of claim 3 wherein $R^4$ and $R^6$ are hydrogen and $R^5$ is amino.

5. The compound of claim 2 wherein Y is $CR^{10}$.

6. The compound of claim 5 wherein $R^4$ and $R^6$ are hydrogen and $R^5$ is amino.

7. The compound of claim 1 wherein B is a pyrimidine base of the structural formula:

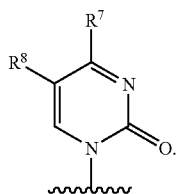

8. The compound of claim 7 wherein $R^8$ is hydrogen and $R^7$ is amino.

9. The compound of claim 1 wherein $R^2$ is phenyl unsubstituted or substituted with one to three substituents independently selected from $R^9$.

10. The compound of claim 1 wherein $R^2$ is $C_{1-6}$ alkyl unsustituted or substituted with one to three substituents independently selected from fluoro, hydroxy, carboxy, and $C_{1-4}$ alkoxy.

11. The compound of claim 1 wherein $R^3$ is hydrogen, $C_{1-6}$ alkylcarbonyl, $C_{3-6}$ cycloalkylcarbonyl, phenylcarbonyl, or heteroarylcarbonyl wherein phenylcarbonyl and heteroarylcarbonyl are unsubstituted or substituted with one to three substituents independently selected from $R^9$ and wherein alkylcarbonyl and cycloalkylcarbonyl are unsubstituted or substituted with one to three substituents independently selected from fluorine, hydroxy, carboxy, $C_{1-4}$ alkoxy, amino, $C_{1-4}$ alkylamino, and di($C_{1-4}$ alkyl)amino.

12. A compound which is selected from the group consisting of:

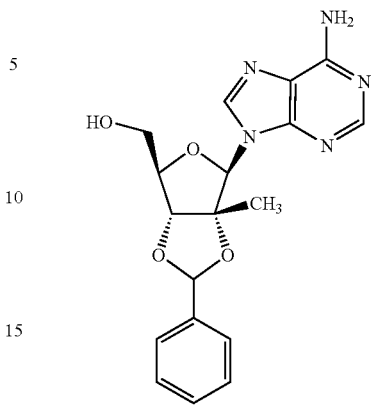

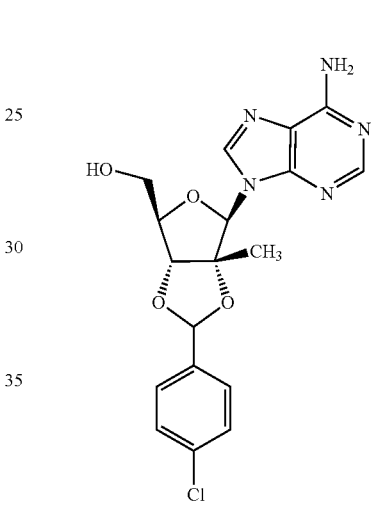

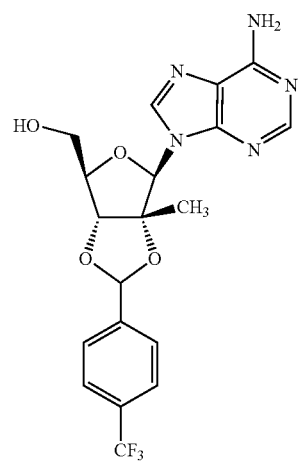

47
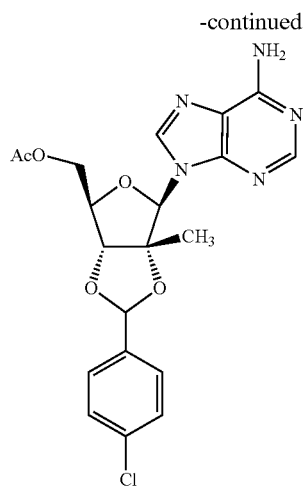
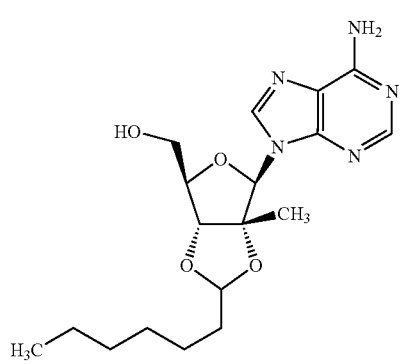
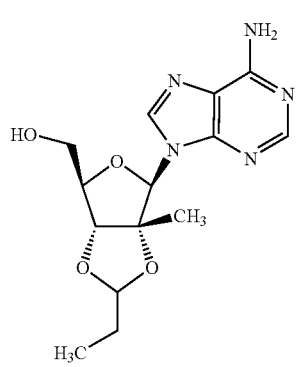
48
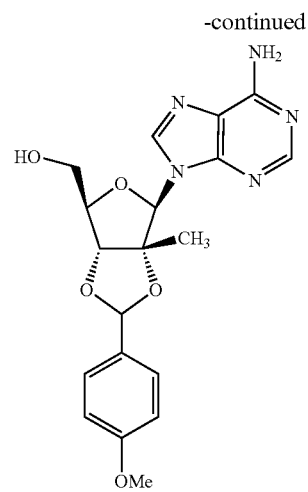
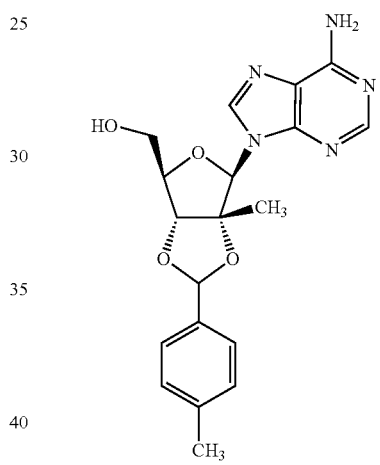
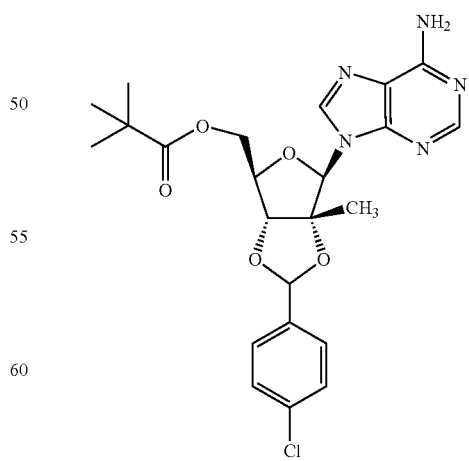

-continued

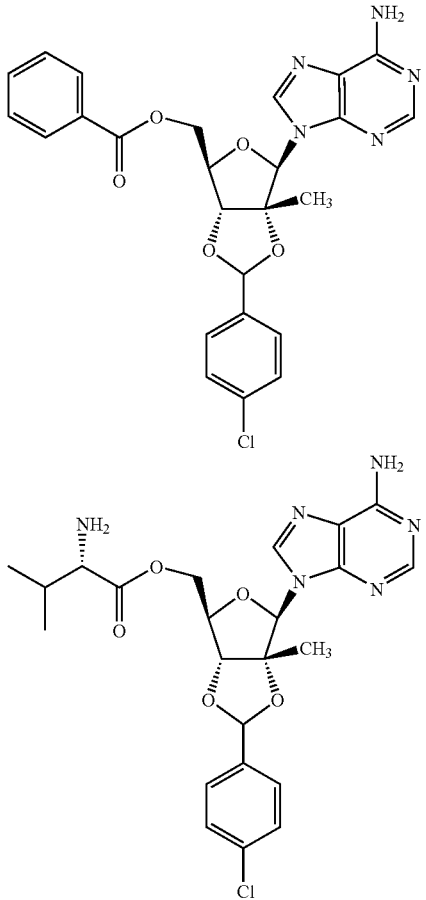

and

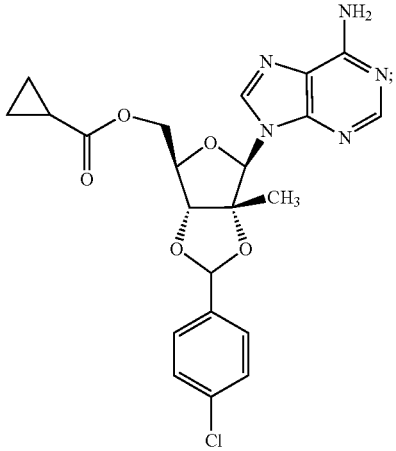

or a pharmaceutically acceptable salt thereof.

13. A pharmaceutical composition comprising an effective amount of a compound of claim 1, or a pharmaceutically acceptable salt thereof, and a pharmaceutically acceptable carrier.

14. A method for treating hepatitis C virus infection in a mammal, which comprises administering to the mammal a therapeutically effective amount of a compound of claim 1, or a pharmaceutically acceptable salt thereof.

15. A method for treating hepatitis C virus infection in a mammal, which comprises administering to the mammal a pharmaceutical composition comprising a therapeutically effective amount of a compound of claim 1, or a pharmaceutically acceptable salt thereof, and a pharmaceutically acceptable carrier.

* * * * *

UNITED STATES PATENT AND TRADEMARK OFFICE
CERTIFICATE OF CORRECTION

PATENT NO. : 7,632,821 B2
APPLICATION NO. : 11/990051
DATED : December 15, 2009
INVENTOR(S) : Butora et al.

It is certified that error appears in the above-identified patent and that said Letters Patent is hereby corrected as shown below:

On Title Page, in the third line of Part (86), replace "Feb. 1, 2008" with --Feb. 5, 2008--.

Signed and Sealed this

Fifteenth Day of June, 2010

David J. Kappos
*Director of the United States Patent and Trademark Office*